(12) United States Patent
Yamanaka et al.

(10) Patent No.: US 11,363,873 B2
(45) Date of Patent: Jun. 21, 2022

(54) COSMETIC

(71) Applicant: TAIKI CORP., LTD., Osaka (JP)

(72) Inventors: Reiko Yamanaka, Osaka (JP); Yuka Hara, Osaka (JP); Giae Kim, Osaka (JP); Yukiko Doi, Osaka (JP)

(73) Assignee: TAIKI CORP., LTD., Osaka (JP)

( * ) Notice: Subject to any disclaimer, the term of this patent is extended or adjusted under 35 U.S.C. 154(b) by 842 days.

(21) Appl. No.: 16/314,751

(22) PCT Filed: Jul. 4, 2017

(86) PCT No.: PCT/JP2017/024509
§ 371 (c)(1),
(2) Date: Jan. 2, 2019

(87) PCT Pub. No.: WO2018/008641
PCT Pub. Date: Jan. 11, 2018

(65) Prior Publication Data
US 2019/0150588 A1 May 23, 2019

(30) Foreign Application Priority Data
Jul. 7, 2016 (JP) .............................. JP2016-134772

(51) Int. Cl.
*A45D 34/04* (2006.01)
*D04H 1/435* (2012.01)
(Continued)

(52) U.S. Cl.
CPC ................ *A45D 34/04* (2013.01); *A61K 8/02* (2013.01); *A61Q 1/02* (2013.01); *B32B 5/26* (2013.01);
(Continued)

(58) Field of Classification Search
CPC ...... A45D 34/04; D04H 1/435; D04H 1/4374; D04H 1/5412; A61Q 1/02; B32B 5/26;
(Continued)

(56) References Cited

U.S. PATENT DOCUMENTS 9,498,043 B2 * 11/2016 Nishimura ............. A45D 34/04
10,413,037 B2 * 9/2019 Yamanaka ........... D04H 1/5418
(Continued)

FOREIGN PATENT DOCUMENTS

JP  2000-157333 A  6/2000
JP  2006-233364 A  9/2006
(Continued)

OTHER PUBLICATIONS

English translation of Japanese Patent Application Publication No. 2006-233364 obtained from the European Patent Office (Year: 2006).*

(Continued)

*Primary Examiner* — Jeremy R Pierce
(74) *Attorney, Agent, or Firm* — WHDA, LLP

(57) ABSTRACT

An elastic body for holding a cosmetic, which can suppress that the cosmetic included in the elastic body for holding a cosmetic is taken out from the elastic body in a large amount at a time at the initial stage of use, wherein the elastic body for holding a cosmetic has a three-dimensional structure, (Continued)

and at least a dense fibrous surface layer and a sparse fibrous substrate; a cosmetic-containing elastic body in which a cosmetic is included in the elastic body for holding cosmetic; and a cosmetic article having the cosmetic-containing elastic body.

10 Claims, 14 Drawing Sheets

(51) Int. Cl.
*D04H 1/4374* (2012.01)
*A61Q 1/02* (2006.01)
*A61K 8/02* (2006.01)
*B32B 5/26* (2006.01)
*D04H 1/541* (2012.01)

(52) U.S. Cl.
CPC .............. *B32B 5/273* (2021.05); *D04H 1/435* (2013.01); *D04H 1/4374* (2013.01); *D04H 1/5412* (2020.05); *B32B 2262/124* (2021.05); *B32B 2307/72* (2013.01)

(58) Field of Classification Search
CPC ................ B32B 5/273; B32B 2307/72; B32B 2262/124
See application file for complete search history.

(56) References Cited

U.S. PATENT DOCUMENTS

| | | |
|---|---|---|
| 2009/0151849 A1 | 6/2009 | MacDonald et al. |
| 2009/0318050 A1 | 12/2009 | Okaya |
| 2014/0023689 A1 | 1/2014 | Kim et al. |
| 2015/0079862 A1 | 3/2015 | Jeong et al. |

FOREIGN PATENT DOCUMENTS

| | | |
|---|---|---|
| JP | 2010-131055 A | 6/2010 |
| JP | 5465357 B2 | 4/2014 |
| JP | 2015-513987 A | 5/2015 |
| WO | 2014/022988 A1 | 2/2014 |

OTHER PUBLICATIONS

Extended (Supplementary) European Search Report dated Feb. 3, 2020, issued in counterpart EP Application No. 17824244.2. (7 pages).

International Search Report dated Aug. 8, 2017, issued in counterpart application No. PCT/JP2017/024509 (2 pages).

* cited by examiner

COSMETIC

CROSS-REFERENCE TO RELATED APPLICATIONS

The present application claims priority under 35 U.S.C. 371 to International Application Serial No. PCT/JP2017/024509, filed on Jul. 4, 2017, which in turn claims priority to Japanese Patent Application No. 2016-134772, filed on Jul. 7, 2016.

TECHNICAL FIELD

The present invention relates to a cosmetic article. More specifically, the present invention relates to an elastic body for holding a cosmetic, which is used for holding the cosmetic; a cosmetic-containing elastic body in which the cosmetic is included in the elastic body for holding the cosmetic; and a cosmetic article having the cosmetic-containing elastic body. The cosmetic-containing elastic body according to the present invention can be suitably used in, for example, various cosmetic articles such as a puff which is used in applying the cosmetic to a skin.

BACKGROUND ART

In recent years, a cosmetic article in which, for example, a liquid cosmetic such foundation is held in a cosmetic container such as a compact has been put on the market. The cosmetic container has a container body and a lid, and an elastic body for holding the liquid cosmetic is included in the container body. As the above-mentioned elastic body for holding the liquid cosmetic, a polyurethane foam, in particular, a polyether-based urethane foam has been used from the viewpoint of improvement in stability when the cosmetic is impregnated into the foam, impregnation property and cushioning property when the cosmetic is taken out from the foam (see, for example, Patent Document 1).

According to the polyether-based urethane foam, a liquid cosmetic can be included in the inside thereof. However, the polyether-based urethane foam has some drawbacks such as consumption of the cosmetic in a short period of time when the cosmetic included in the polyurethane foam is taken out from the polyurethane foam by using a puff or the like because the cosmetic is transferred to the puff in a large amount at a time at the initial stage of use, and swelling of the polyurethane foam due to chemicals included in the cosmetic.

PRIOR ART DOCUMENTS

Patent Document

Patent Document 1; Japanese patent No. 5465357

SUMMARY OF THE INVENTION

Problem to be Solved by the Invention

The present invention has been made in view of the above-mentioned prior art. An object of the present invention is to provide an elastic body for holding a cosmetic, which can suppress that the cosmetic included in the elastic body for holding the cosmetic is taken out from the elastic body in a large amount at a time at the initial stage of use; a cosmetic-containing elastic body in which the cosmetic is included in the elastic body for holding the cosmetic; and a cosmetic article having the cosmetic-containing elastic body.

Means for Solving the Problem

The present invention relates to
(1) an elastic body for holding a cosmetic, having a three-dimensional structure, wherein the elastic body has at least a dense fibrous surface layer and a sparse fibrous substrate;
(2) the elastic body for holding the cosmetic according to the above-mentioned item (1), wherein the dense fibrous surface layer and the sparse fibrous substrate are united into one body, or the dense fibrous surface layer is placed on the sparse fibrous substrate;
(3) a cosmetic-containing elastic body including the elastic body for holding the cosmetic according to the above-mentioned item (1) or (2) and a cosmetic, in which the cosmetic is included in the elastic body for holding the cosmetic; and
(4) the cosmetic article having the cosmetic-containing elastic body according to the above-mentioned item (3).

Effect of the Invention

The elastic body for holding the cosmetic according to the present invention can suppress that the cosmetic included in the elastic body for holding the cosmetic is taken out from the elastic body in a large amount at a time at the initial stage of use. The cosmetic-containing elastic body according to the present invention can suppress that the cosmetic included in the elastic body for holding the cosmetic is taken out from the elastic body in a large amount at a time at the initial stage of use because the cosmetic-containing elastic body has the above-mentioned elastic body for holding the cosmetic. The cosmetic article according to the present invention can suppress that the cosmetic included in the elastic body for holding the cosmetic is taken out from the elastic body in a large amount at a time at the initial stage of use because the cosmetic article has the above-mentioned cosmetic-containing elastic body.

MODES FOR CARRYING OUT THE INVENTION

Figure 1:
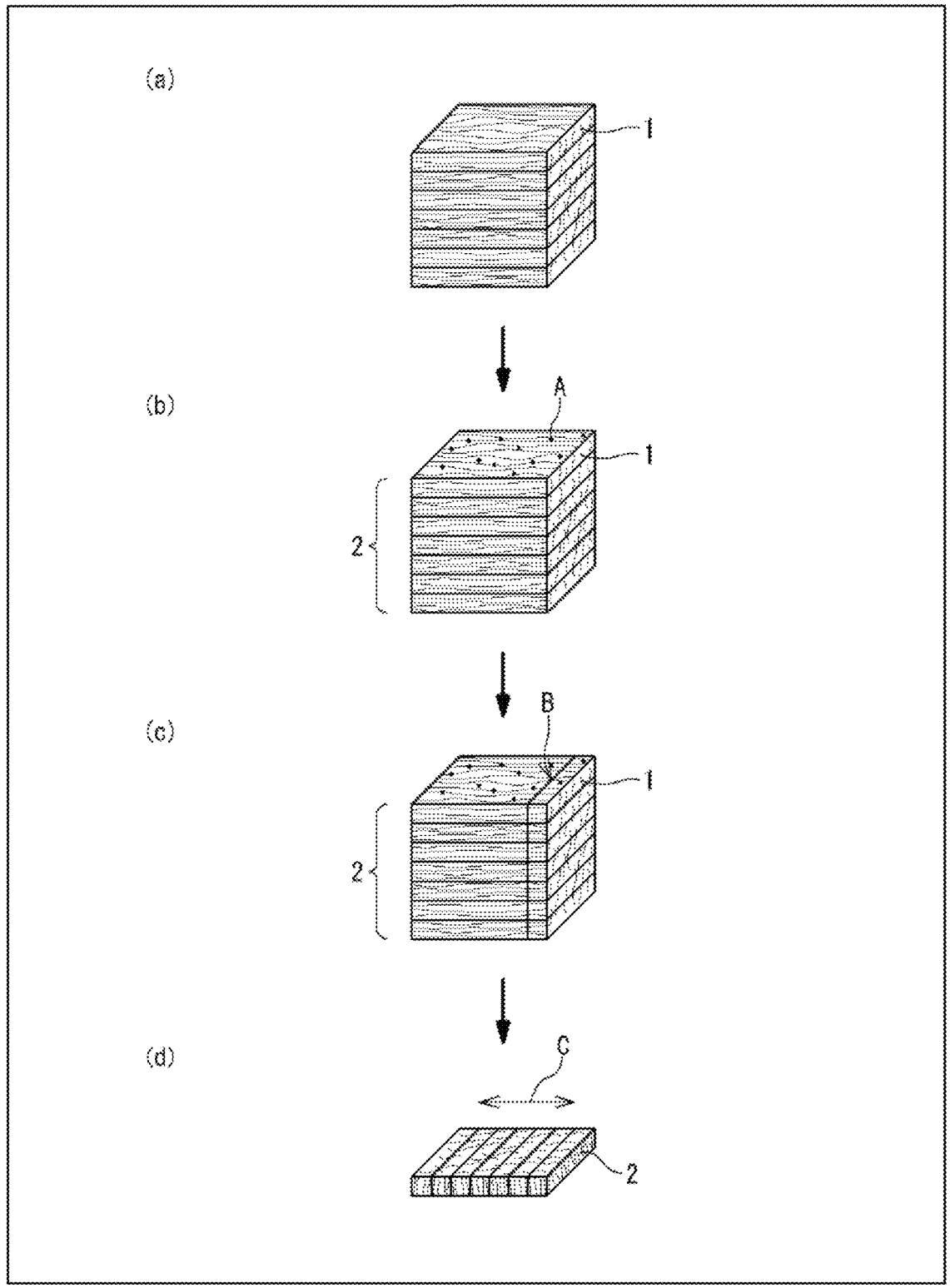
FIG. 1 is a schematic explanation view showing one embodiment of a method for producing a web sheet which is used in producing the elastic body for holding the cosmetic according to the present invention.

As described above, the elastic body for holding a cosmetic according to the present invention is an elastic body for holding a cosmetic, having a three-dimensional structure, and the elastic body has characteristics in that the elastic body has at least a dense fibrous surface layer and a sparse fibrous substrate.

Since the elastic body for holding the cosmetic according to the present invention has the above-mentioned structure, the elastic body can suppress that the cosmetic included in the elastic body is taken out from the elastic body in a large amount at a time at the initial stage of use. In addition, when the elastic body for holding the cosmetic according to the present invention is used, the cosmetic can be taken out from the elastic body in an amount appropriate for one use from the initial use thereof, therefore the number of times for repeatedly using the cosmetic can be increased.

In the elastic body for holding the cosmetic according to the present invention, a conjugated fiber can be used as a raw material of the dense fibrous surface layer and the sparse fibrous substrate.

The conjugated fiber includes, for example, a core-shell conjugated fiber, a side-by-side conjugated fiber, an sea-island conjugated fiber and the like, and the present invention is not limited to only those exemplified ones. Among them, the core-shell conjugated fiber is preferred from the viewpoint of efficient integration of contacted portions between constituent fibers, and the side-by-side conjugated fiber is preferred when crimp of the fiber is generated by heating.

The conjugated fiber can be composed of plural resins. Representative conjugated fiber includes a conjugated fiber in which two kinds of a resin are used. For example, when two kinds of the resin used in the conjugated fiber are a resin A and a resin B, it is preferred that the melting point of the resin A is lower than the melting point of the resin B. The melting point of the resin A is preferably 20° C. or more lower than the melting point of the resin B, more preferably 30° C. or more lower than the melting point of the resin B, from the viewpoint of prevention of the conjugated fiber from permanent setting due to fatigue. The melting point of the resin A is preferably 130 to 220° C. from the viewpoint of prevention of the conjugated fiber from permanent setting due to fatigue, and firm integration of contacted portions between constituent fibers by the resin A.

Incidentally, when the melting temperature of the resin A, the melting temperature of the resin B, and the melting temperature of a synthetic fiber described later cannot be accurately determined, the melting temperature is replaced with a softening temperature thereof.

The resin A includes, for example, a polyester, a thermoplastic elastomer and the like, and the present invention is not limited only to those exemplified ones.

The polyester includes, for example, polyethylene terephthalate, polytrimethylene terephthalate, polybutylene terephthalate, polyhexamethylene terephthalate, polytetramethylene terephthalate, poly 1,4-dimethylcyclohexane terephthalate, polyhydrolactone and the like, and the present invention is not limited only to those exemplified ones. These polyesters can be used alone respectively, or at least two kinds thereof can be used in combination. Among these thermoplastic polyesters, polyethylene terephthalate, polytrimethylene terephthalate, polybutylene terephthalate and polyhexamethylene terephthalate are preferred because these polyesters are excellent in light resistance.

The thermoplastic elastomer includes, for example, a polyester-based elastomer, a polyurethane-based elastomer and the like. Among the thermoplastic elastomers, the polyester-based elastomer is preferred from the viewpoint of improvement in light resistance of the elastic body for holding the cosmetic according to the present invention.

The polyester-based elastomer includes, for example, a polyester elastomer such as a polyethylene terephthalate elastomer, a polyether-ester block copolymer in which the polyester is used as a hard segment, and a poly(alkylene oxide) is used as a soft segment, and the like. The polyether-ester block copolymer can be prepared by reacting a dicarboxylic acid with a diol and a poly(alkylene oxide) glycol.

The above-mentioned dicarboxylic acid includes, for example, aromatic dicarboxylic acids such o-phthalic acid, m-phthalic acid, terephthalic acid, naphthalene-2,6-dicarboxylic acid, naphthalene-2,7-dicarboxylic acid, diphenyl-4,4'-dicarboxylic acid, diphenoxyethane dicarboxylic acid and sodium 3-sulfoisophthalate; alicyclic dicarboxylic acids such as 1,4-cyclohexanedicarboxylic acid; aliphatic dicarboxylic acids such as succinic acid, oxalic acid, adipic acid, sebacic acid, dodecanedioic acid and a dimer acid; and the like. The present invention is not limited only to those exemplified ones. These dicarboxylic acids can be used alone respectively, or at least two kinds thereof can be used in combination.

The above-mentioned diol includes, for example, aliphatic diols such as ethylene glycol, trimethylene glycol, tetramethylene glycol, pentamethylene glycol, hexamethylene glycol, 1,4-butanediol, neopentyl glycol and decamethylene glycol; alicyclic diols such as 1,1-cyclohexanedimethanol, 1,4-cyclohexanedimethanol and tricyclodecane dimethanol, and the present invention is not limited only to those exemplified ones. These diols can be used alone respectively, or at least two kinds thereof can be used in combination.

The above-mentioned poly(alkylene oxide) glycol includes, for example, polyethylene glycol, poly(1,2-propylene oxide) glycol, poly(1,3-propylene oxide) glycol, poly (tetramethylene oxide) glycol, ethylene oxide-propylene oxide copolymer, ethylene oxide-tetrahydrofuran copolymer and the like, and the present invention is not limited only to those exemplified ones. These poly(alkylene oxide) glycols can be used alone respectively, or at least two kinds thereof can be used in combination. It is preferred that the number average molecular weight of the poly(alkylene oxide) glycol is usually 400 to 5000 or so.

The intrinsic viscosity of the polyester-based elastomer is preferably 0.8 to 1.7, and more preferably 0.9 to 1.5, from the viewpoint of firm integration of the contact portions between the constituent fibers by the resin A.

The polyurethane-based elastomer can be prepared, for example, by polymerizing a polyol and a diisocyanate in the presence of a chain extender.

The polyol includes, for example, polyols such as dihydroxy polyether, dihydroxypolyester, dihydroxypolycarbonate and dihydroxypolyesteramide, each of which has a molecular weight of 500 to 6000 or so, and the like. The present invention is not limited only to those exemplified ones. These polyols can be used alone respectively, or at least two kinds thereof can be used in combination.

The diisocyanate includes, for example, diisocyanates such as diphenylmethane diisocyanate, tolylene diisocyanate, isophorone diisocyanate, hydrogenated diphenylmethane diisocyanate, xylylene diisocyanate, diisocyanate methylcaproate and hexamethylene diisocyanate, each of which has a molecular weight of 500 or less, and the like. The present invention is not limited only to those exemplified ones. These diisocyanates can be used alone respectively, or at least two kinds thereof can be used in combination.

The chain extender includes, for example, ethylene glycol, amino alcohol, bis-hydroxyethoxybenzene, 1,4-butanediol and the like, and the present invention is not limited only to those exemplified ones. These chain extenders can be used alone respectively, or at least two kinds thereof can be used in combination.

As the thermoplastic elastomer, a polyether-polyester having a polybutylene terephthalate as a hard segment and a polyoxybutylene glycol as a soft segment can be used from the viewpoint of firm integration of the contact portions between the constituent fibers by the resin A.

In the above-mentioned hard segment, a part of an acid component used as a raw material of the polybutylene terephthalate can be replaced with an acid such as dicarboxylic acid other than terephthalic acid, or an oxycarboxylic acid within a scope which would not hinder an object of the present invention. In addition, a part of butylene glycol used as a raw material of polybutylene glycol can be replaced with a polyhydric alcohol other than butylene glycol within a scope which would not hinder an object of the present invention.

In the above-mentioned soft segment, a part of butylene glycol used as a raw material of polybutylene glycol can be replaced with a polyhydric alcohol other than butylene glycol within a scope which would not hinder an object of the present invention.

The resin B includes, for example, a thermoplastic polyester and the like, and the present invention is not limited only to the exemplified one.

The thermoplastic polyester includes, for example, polyethylene terephthalate, polytrimethylene terephthalate, polybutylene terephthalate, polyhexamethylene terephthalate, polytetramethylene terephthalate, poly 1,4-dimethylcyclohexane terephthalate, polyhydrolactone and the like, and the present invention is not limited only to those exemplified ones. These thermoplastic polyesters can be used alone respectively, or at least two kinds thereof can be used in combination. Among the thermoplastic polyesters, polyethylene terephthalate, polytrimethylene terephthalate, polybutylene terephthalate and polyhexamethylene terephthalate are preferred, because these polyesters are excellent in light resistance.

The melting temperature of the resin B is preferably 20° C. or more higher than the melting temperature of the resin A, and more preferably 30° C. or more higher than the melting temperature of the resin A, from the viewpoint of prevention of the conjugated fiber from permanent setting due to fatigue. The melting temperature of the resin B is preferably 150 to 270° C., and more preferably 160 to 270° C., from the viewpoint of prevention of the conjugated fiber from permanent setting due to fatigue, and firm integration of the contact portions between the constituent fibers by the resin A.

It is preferred that the resin A is the polyester or the polyester-based elastomer, and the resin B is the thermoplastic polyester, from the viewpoint of improvement in light resistance, prevention of the conjugated fiber from permanent setting due to fatigue, and firm integration of the contact portions between the constituent fibers by the resin A.

It is preferred that the surface area of the conjugated fiber is composed of 30 to 70% of the resin A and 70 to 30% of the resin B from the viewpoint of prevention of the conjugated fiber from permanent setting due to fatigue, and firm integration of the contact portions between the constituent fibers by the resin A.

The conjugated fiber includes the resin A and the resin B having a melting temperature higher than the melting temperature of the resin A, and may contain a resin other than the resin A and the resin B within a scope which would not hinder an object of the present invention.

When the conjugated fiber is the core-shell conjugated fiber or the side-by-side conjugated fiber, two kinds of the resin of the resin A and the resin B are usually used in the conjugated fiber. When the conjugated fiber is the sea-island conjugated fiber, 2 to 4 kinds of the resin including the resin A and the resin B, preferably 2 or 3 kinds of the resin including the resin A and the resin B, and more preferably the resin A and the resin B are usually used in the conjugated fiber.

In the core-shell conjugated fiber, the resin B is used in the core, and the resin A is used in the shell, from the viewpoint of firm integration of the contact portions between the constituent fibers by the resin A.

In the core-shell conjugated fiber, it is preferred that the core component is not exposed to the surface of the conjugated fiber. In addition, it is more preferred that the center of the core component in the direction of the diameter of the fiber is coincident with the center of the shell component in the direction of the diameter of the fiber. In the core-shell conjugated fiber, a core-shell structure can be formed in a concentric core-sheath structure or in an eccentric core-sheath structure. The conjugated fiber having a core-shell structure, in which the core-shell structure is eccentrically formed, is suitable for uses which require crimps, because the conjugated fiber generates crimps when the conjugated fiber is heated. The shape of the cross-section of the core-sheath type conjugated fiber includes, for example, a circular shape, a triangle shape, a polygonal shape such as a quadrangle shape, an ellipse shape and an oval shape, and the present invention is not limited only to those exemplified ones. Among these shapes, the circular shape is preferred. In addition, in the core-sheath type conjugated fiber, it is preferred that the volume ratio of the core component to the sheath component is 30:70 to 70:30 from the viewpoint of improvement in strength of a single fiber and firm integration of the contact portions between the constituent fibers by the resin A.

When the conjugated fiber is the core-shell conjugated fiber, the core-shell conjugated fiber can be produced by, for example, heating to melt the resin B which constitutes a core component and the resin A which constitutes a shell component, introducing the molten resin B and the molten resin A into a composite spinning apparatus for producing a core-shell conjugated fiber, extruding and spinning the molten resin B and the molten resin A from a core-sheath type composite nozzle. Incidentally, when the resin A and the resin B are heated to melt, for example, a single screw extruder, a biaxial extruder, a kneader and the like can be used. In addition, as the core-sheath type composite nozzle, for example, a core-sheath type composite nozzle in which pores of the nozzle are arranged in a zigzag arrangement or an annular arrangement can be used.

Next, a spun core-shell conjugated fiber can be cooled to solidify by, for example, blowing cool air to the core-shell conjugated fiber.

The fineness of the conjugated fiber is preferably 0.5 to 15 deniers, and more preferably 1 to 10 deniers, from the viewpoint of obtaining of the elastic body for holding the cosmetic, from which the cosmetic included in the elastic body for holding the cosmetic can be efficiently taken out to the outside, and which is excellent in mechanical strength. Incidentally, in the present invention, the fineness of a fiber means mass (g) of the fiber (filament) per 9000 m of the fiber length.

The fiber length of the conjugated fiber is preferably 20 to 150 mm or so from the viewpoint of obtaining of the elastic body for holding the cosmetic, from which the cosmetic included in the elastic body for holding the cosmetic can be efficiently taken out to the outside, and which is excellent in mechanical strength.

To the conjugated fiber, for example, processing such as antibacterial processing or antimicrobial processing can be applied as occasion demands from the viewpoint of preservation of the cosmetic used in the cosmetic article. To the processing, various methods can be applied, and the present invention is not limited to the methods.

Incidentally, the elastic body for holding the cosmetic according to the present invention contains the conjugated fiber as a constituent fiber. The elastic body for holding the cosmetic can be composed only of the conjugated fiber. Alternatively, the elastic body for holding the cosmetic can be composed of the conjugated fiber and a fiber other than the conjugated fiber.

The fiber other than the conjugated fiber includes, for example, natural fibers such as cotton, linen and silk; regenerated fibers such as rayon; synthetic fibers; and the like. The present invention is not limited to those exemplifies ones. Among these fibers other than the conjugated fiber, the synthetic fiber is preferred from the viewpoint of obtaining of the elastic body for holding the cosmetic, which can supply the cosmetic to a puff or the like while the amount of the cosmetic included in the elastic body is gradually reduced, and which is excellent in mechanical strength.

The synthetic fiber includes, for example, polyester fibers such as a polyethylene terephthalate fiber, a polybutylene terephthalate fiber and a polytrimethylene terephthalate fiber, a polyvinyl chloride fiber, a polyvinylidene chloride fiber, a polypropylene fiber, a polyvinyl alcohol fiber, polyamide fibers represented by nylon-6, a polyimide fiber, a polyamide-imide fiber, a cellulose acetate fiber and the like, and the present invention is not limited only to those exemplified ones. These fibers can be used alone respectively, or at least two kinds thereof can be used in combination. Among these synthetic fibers, the polyester fiber and the polyamide fiber are preferred, and the polyester fiber is more preferred, from the viewpoint of obtaining of the elastic body for holding the cosmetic, which can supply the cosmetic to a puff or the like while the amount of the cosmetic included in the elastic body is gradually reduced, and which is excellent in light resistance.

To the synthetic fiber, for example, processing such as antibacterial processing or antimicrobial processing can be applied as occasion demands from the viewpoint of preservation of the cosmetic and the like used in the cosmetic article. To the processing, various methods can be applied, and the present invention is not limited to the methods.

The melting temperature of the synthetic fiber is preferably 20° C. or more higher than the melting temperature of the resin A, and more preferable 30° C. or more higher than the melting temperature of the resin A, from the viewpoint of prevention of the conjugated fiber from permanent setting due to fatigue. The melting temperature of the synthetic fiber is preferably 150 to 270° C., and more preferably 160 to 270° C., from the viewpoint of prevention of the conjugated fiber from permanent setting due to fatigue, and efficient thermal fusion of the conjugated fiber and the synthetic fiber at the intersection of the conjugated fiber and the synthetic fiber.

The fineness of the synthetic fiber is preferably 0.5 to 15 deniers, and more preferably 1 to 10 deniers, from the viewpoint of obtaining of the elastic body for holding the cosmetic, from which the cosmetic included in the elastic body for holding the cosmetic can be efficiently taken out to the outside.

The fiber length of the synthetic fiber is preferably 20 to 150 mm or so from the viewpoint of obtaining of the elastic body for holding the cosmetic, from which the cosmetic included into the elastic body can be efficiently taken out to the outside, and which is excellent in mechanical strength.

In the present invention, it is preferred that the conjugated fiber is used together with the synthetic fiber as the other fiber, more preferred that the conjugated fiber is used together with the polyester fiber or the polyamide fiber as the synthetic fiber, and furthermore preferred that the conjugated fiber is used together with the polyester fiber, from the viewpoint of obtaining of the elastic body for holding the cosmetic, from which the cosmetic included in the elastic body can be efficiently taken out to the outside, and which is excellent in mechanical strength.

The mass ratio of the conjugated fiber to the synthetic fiber (conjugated fiber/synthetic fiber) is preferably 10/90 to 100/0, and more preferably 30/70 to 80/20, from the viewpoint of efficient thermal fusion of the conjugated fiber and the synthetic fiber at the intersection of the conjugated fiber and the synthetic fiber, and obtaining of the elastic body for holding the cosmetic, which can supply the cosmetic to a puff and the like while the amount of the cosmetic included in the elastic body is gradually reduced.

A method for producing a web sheet which is used in producing the elastic body for holding the cosmetic will be explained below in accordance with drawings. However, the present invention is not limited only to the embodiments described in the drawings. Incidentally, in the followings, although an example of a combined use of the conjugated fiber and the synthetic fiber is described, the conjugated fiber can be used solely. Alternatively, the conjugated fiber and the fiber other than the synthetic fiber can be used in combination.

FIG. 1 is a schematic explanation view showing one embodiment of a method for producing a web sheet which is used in producing the elastic body for holding the cosmetic according to the present invention.

As shown in FIG. 1(a), a web 1 is laminated. The web 1 can be produced, for example, by disintegrating the conjugated fiber and the synthetic fiber, weighing both so as to have a predetermined ratio, and mixing the conjugated fiber with the synthetic fiber so as to form a uniform composition. It is preferred that the thickness of the formed web is appropriately adjusted in accordance with a size of the elastic body for holding the cosmetic being used.

Next, for example, the web 1 is placed between two flat plates (not shown in the figure), and press the web 1 so that the web 1 has a predetermined thickness as required. Under this condition, the web 1 is heated to a temperature which is equal to or higher than the melting temperature of the resin A which constitutes the conjugated fiber included in the web 1, and which is lower than the melting temperatures of the resin B which constitutes the conjugated fiber and the synthetic fiber, to melt the resin A, and the constituting fibers including the conjugated fiber and the synthetic fiber are united into one body at the contacting portions thereof by the molten resin A. Thereby, a web sheet 2 can be obtained as shown in FIG. 1(b). At that time, as occasion demands, massive (ameboid) fused portions made of the resin A can be formed by putting the web sheet 2 in a mold so as to have a predetermined density, heating the web sheet 2 in the same manner as mentioned above to melt the resin A, and fusing the intersection of the constituting fibers by the molten resin A. The above-mentioned fused portions are shown by a symbol A in FIG. 1(b).

In the web sheet 2 obtained in the above, the intersected portions of the constituting fibers are bonded in a point-like shape by the molten resin A, and the fibers being bonded are arranged in the plane direction of the web sheet 2.

Next, the web sheet 2 obtained in the above is cut in the vertical direction as shown by an arrow B in FIG. 1(c). The cut web sheet 2 is arranged so that the cut face forms an upper surface or a lower surface as shown in FIG. 1(d). Since the web sheet 2 has a structure like a jungle gym in the thickness direction, the web sheet 2 shows high repulsion against a pressure from the upper face of the web sheet 2. Accordingly, it is considered that the web sheet 2 is excellent in cushioning property, and also is excellent in resistance against "permanent setting due to fatigue".

Incidentally, when the web sheet 2 is produced by laminating the conjugated fiber and the synthetic fiber so that both of the fibers are arranged to be parallel in the longitudinal direction of the fibers in mixing the conjugated fiber with the synthetic fiber, a stripe showing that both of the conjugated fiber and the synthetic fiber are arranged to be parallel appears in the case that the web sheet 2 is elongated in the direction of an arrow C shown in FIG. 1(d). The stripe becomes an index showing that the web sheet 2 has been produced by the above-mentioned method.

Next, the elastic body for holding the cosmetic according to the present invention can be produced by using the web sheet 2 obtained in the above.

The elastic body for holding the cosmetic according to the present invention includes, for example, (1) an elastic body for holding the cosmetic in which the dense fibrous surface layer and the sparse fibrous substrate are united into one body (hereinafter referred to "elastic body for holding cosmetic A"), (2) an elastic body for holding the cosmetic in which the dense fibrous surface layer is placed on the sparse fibrous substrate (hereinafter referred to "elastic body for holding cosmetic B")

and the like, and the present invention is not limited only to those elastic bodies for holding the cosmetic.

The above-mentioned elastic body for holding cosmetic A can be produced by a method including uniting the dense fibrous surface layer made of the above-mentioned web sheet and the sparse fibrous substrate made of the above-mentioned web sheet into one body (hereinafter referred to as "method A"). The above-mentioned elastic body for holding cosmetic B can be produced by a method including placing the dense fibrous surface layer made of the above-mentioned web sheet on the sparse fibrous substrate made of the above-mentioned web sheet (hereinafter referred to as "method B"). The present invention is not limited only to those methods.

In the above-mentioned method A, the elastic body for holding cosmetic A in which the dense fibrous surface layer and the sparse fibrous substrate are united into one body can be produced by pressing the above-mentioned web sheet from the cut face side, heating the pressed face of the web sheet under the condition of compressing to melt the resin A, thereafter cooling the web sheet, and releasing the pressure. The density of the dense fibrous surface layer can be controlled by appropriately adjusting a heating temperature, a pressing period of time and a pressure when pressing the web sheet. Incidentally, the unification of the dense fibrous surface layer and the sparse fibrous substrate into one body means that the dense fibrous surface layer is directly formed on the surface of the sparse fibrous substrate.

When the web sheet is pressed, and its pressed face is heated under the condition of compressing the pressed face, the heating temperature is adjusted to a temperature at which the resin A is molten or higher. It is preferred that the heating temperature is 150° C. or higher from the viewpoint of formation of a dense surface structure by joining the fibers with the resin A. The heating period of time and the pressure in compressing can be appropriately adjusted so that the web sheet has a predetermined thickness. When the web sheet is pressed, and its pressed face is heated under the condition of compressing the pressed face, the dense fibrous surface layer can be formed by, for example, heating the web sheet at a temperature around the melting temperature of the resin A for several minutes. In addition, the dense fibrous surface layer also can be formed by heating the web sheet at a high temperature (a temperature equal to or higher than the melting temperature of the resin other than the resin A) for several ten seconds.

In the elastic body for holding cosmetic A, it is preferred that the thickness of the dense fibrous surface layer is 50 μm to 5 mm or so from the viewpoint of inhibition of removal of the cosmetic included in the elastic body at a time at the initial stage of use in a large amount. In addition, the thickness of the sparse fibrous substrate is preferably 500 μm to 10 cm or so, and more preferably 5 mm to 20 mm, from the viewpoint of increase of the amount of the cosmetic in the sparse fibrous substrate.

According to the above-mentioned method A, for example, the elastic body for holding cosmetic A having an overall thickness of 11 mm and a thickness of the dense fibrous surface layer of 1.5 mm can be produced by pressing the sparse fibrous substrate having a thickness of 16 mm, heating its pressed face under the condition of compressing, cooling the fibrous substrate, and releasing the pressure.

In the elastic body for holding cosmetic A, it is preferred that the density of the dense fibrous surface layer is 45 to 60 kg/m$^3$ or so, and that the density of the sparse fibrous substrate is 13 to 20 kg/m$^3$ or so, from the viewpoint of inhibition of removal of the cosmetic included in the elastic body for holding cosmetic A at a time at the initial stage of use in a large amount.

In addition, a value obtained by dividing a density of the dense fibrous surface layer by a density of the sparse fibrous substrate (hereinafter referred to "compression ratio") is preferably 2 to 4, and more preferably 2.5 to 3.5, from the viewpoint of inhibition of removal of the cosmetic included in the elastic body for holding cosmetic A at a time at the initial stage of use in a large amount.

The airflow resistance of the dense fibrous surface layer of the elastic body for holding cosmetic A is preferably 0.0125 to 0.0275 kPa-s/m, and more preferably 0.0145 to 0.0255 kPa-s/m, from the viewpoint of inhibition of removal of the cosmetic included in the elastic body for holding cosmetic A at a time at the initial stage of use in a large amount.

In the above-mentioned method B, the elastic body for holding cosmetic B can be obtained by producing the dense fibrous surface layer made of the above-mentioned web sheet and the sparse fibrous substrate separately, and placing the dense fibrous surface layer on the sparse fibrous substrate.

In the elastic body for holding cosmetic B, it is preferred that the thickness of the dense fibrous surface layer is 50 μm to 5 mm or so from the viewpoint of inhibition of removal of the cosmetic included in the elastic body at a time at the initial stage of use in a large amount. In addition, the thickness of the sparse fibrous substrate is preferably 500 μm to 10 cm or so, and more preferably 5 mm to 20 mm, from the viewpoint of increase of the amount of the cosmetic included in the elastic body.

When the dense fibrous surface layer is produced by the above-mentioned method B, the dense fibrous surface layer can be produced by heating a pressed face of the sparse fibrous substrate having a predetermined thickness under the condition of compressing the sparse fibrous substrate from its cut face side, cooling the sparse fibrous substrate, and release the pressure from the sparse fibrous substrate, as well as the above-mentioned method A. In addition, the dense fibrous surface layer also can be produced by heating both surfaces of the sparse fibrous substrate under the condition of compressing the sparse fibrous substrate. For example, when the sparse fibrous substrate having a thickness of 4 to 8 mm is used, the dense fibrous surface layer having a thickness of 2 to 4 mm can be produced by the above-mentioned method B.

In the above-mentioned method B, the elastic body for holding cosmetic B can be produced by placing the dense fibrous surface layer on the sparse fibrous substrate. Incidentally, the concept that the dense fibrous surface layer is placed on the sparse fibrous substrate includes a concept that the dense fibrous surface layer is put on the sparse fibrous substrate, and a concept that the dense fibrous surface layer is joined to the sparse fibrous substrate by means of, for example, an adhesive, thermal fusion or the like to a degree which would not obstruct passing of the cosmetic.

In the above-mentioned method B, when the pressed face is heated under the condition of compressing the sparse fibrous substrate, its heating temperature is preferably a temperature at which the resin A is molten or higher, and more preferably 150° C. or higher, from the viewpoint of formation of a dense surface structure by joining the fibers. Incidentally, it is preferred that the heating period of time and the pressure in compressing are appropriately adjusted so that the fibrous substrate has a predetermined thickness.

In the elastic body for holding cosmetic B, it is preferred that the density of the dense fibrous surface layer is 25 to 45 kg/m$^3$ or so, and that the density of the sparse fibrous substrate is 15 to 22.5 kg/m$^3$ or so, from the viewpoint of inhibition of removal of the cosmetic included in the elastic body for holding cosmetic B at a time at the initial stage of use in a large amount.

In addition, the above-mentioned compression ratio is preferably 1.2 to 2.5, and more preferably 1.3 to 2.0, from the viewpoint of inhibition of removal of the cosmetic included in the elastic body for holding cosmetic B at a time at the initial stage of use in a large amount.

The airflow resistance of the dense fibrous surface layer of the elastic body for holding cosmetic B is preferably 0.01 to 0.045 kPa-s/m, and more preferably 0.01 to 0.04 kPa-s/m, from the viewpoint of inhibition of removal of the cosmetic included in the elastic body for holding cosmetic B at a time at the initial stage of use in a large amount. Incidentally, the above-mentioned airflow resistance means a value when determined on the basis of a method described in the following working examples.

The reason that the elastic body for holding cosmetic A is different in a density, airflow resistance and the like from the elastic body for holding cosmetic B is thought to be based on that the method A is different from the method B. More specifically, this reason is thought be based on that according to the above-mentioned method A, the elastic body for holding cosmetic A is produced by forming the sparse fibrous substrate and the dense fibrous surface layer by using a thick sparse fibrous substrate, whereas according to the above-mentioned method B, the elastic body for holding cosmetic B is produced by using the sparse fibrous substrate and the dense fibrous surface layer. Incidentally, the elastic body for holding cosmetic A and the elastic body for holding cosmetic B, which are produced by any of the methods can inhibit removal of the cosmetic in a large amount at a time at the initial stage of use.

Both of the elastic body for holding cosmetic A and the elastic body for holding cosmetic B can inhibit removal of the cosmetic included in the elastic body for holding the cosmetic in a large amount at a time at the initial stage of use. Among these elastic bodies for holding the cosmetic, the elastic body for holding cosmetic B in which the dense fibrous surface layer is placed on the sparse fibrous substrate is preferred.

In the elastic body for holding cosmetic B, when the cosmetic is included in the sparse fibrous substrate, and the dense fibrous surface layer is placed on the sparse fibrous substrate containing the cosmetic, the elastic body for holding cosmetic B has advantages in that the cosmetic included in the elastic body for holding the cosmetic can be more inhibited from removing in a large amount at a time at the initial stage of use, and that the cosmetic can be gradually removed from the dense fibrous surface layer by a puff or the like.

Thus, the elastic body for holding the cosmetic, having a three dimensional structure can be obtained. In the elastic body for holding the cosmetic according to the present invention, the surface of the elastic body for holding the cosmetic becomes denser by compression processing, and the dense fibrous surface layer has an appropriate thickness. Accordingly, it is considered that the removal amount of the cosmetic is suppressed, and that the cosmetic can be prevented from removing in a large amount at a time at the initial stage of use.

Incidentally, in the present invention, a fibrous layer other than the dense fibrous surface layer and the sparse fibrous substrate, a resin layer or a film can be included in the elastic body for holding the cosmetic within a scope which would not hinder an object of the present invention.

In addition, the elastic body for holding the cosmetic according to the present invention can be used after the elastic body is cut so as to have a desired size and a desired shape as occasion demands. The size and shape of the elastic body for holding the cosmetic cannot be absolutely determined, because they are different according to uses of the elastic body for holding the cosmetic. Accordingly, it is preferred that the size and shape of the elastic body for holding the cosmetic are appropriately adjusted in accordance with the uses of the elastic body for holding the cosmetic.

As one embodiment of the elastic body for holding the cosmetic, there can be cited, for example, a cylindrical elastic body for holding the cosmetic, in which its plane shape is a circler shape having a diameter of 3 to 15 cm or so, and its thickness is 0.5 to 5 cm or so. The elastic body for holding the cosmetic can be suitably used, for example, as an elastic body for holding a liquid cosmetic such as foundation.

The overall density of the elastic body for holding the cosmetic according to the present invention cannot be absolutely determined, because the overall density differs depending on uses of the elastic body for holding the cosmetic, and the like. It is preferred that the overall density of the elastic body for holding the cosmetic is 6 to 50 kg/m$^3$ or so.

Incidentally, in the elastic body for holding the cosmetic according to the present invention, as shown in FIG. 1(d), it is preferred that a web sheet 2 is produced by laminating the conjugated fiber and the synthetic fiber so that both of the conjugated fiber and the synthetic fiber are arranged in parallel in the thickness direction of the web sheet 2, and that each fiber is arranged in parallel in the thickness direction of the elastic body for holding the cosmetic.

The elastic body for holding the cosmetic according to the present invention has a three dimensional structure, and at least the dense fibrous surface layer and the sparse fibrous substrate. Accordingly, the removal amount of the cosmetic included in the elastic body for holding the cosmetic can be more inhibited from the initial stage of use as compared with a conventional polyurethane foam.

When the elastic body for holding the cosmetic according to the present invention is used by pressing with a puff at the time of removal of the cosmetic from the sparse fibrous substrate in which the cosmetic is impregnated, the cosmetic being impregnating in the sparse fibrous substrate is pushed out from the sparse fibrous substrate, and reaches the dense fibrous surface layer. The amount of the cosmetic being pushed out from the dense fibrous surface layer is restricted, because the dense fibrous surface layer has a structure denser than the sparse fibrous substrate. Accordingly, a phenomenon such as removal of the cosmetic in a large amount at a time can be avoided at the initial stage of use, and the cosmetic can be applied to the puff in an amount substantially appropriate for its use even after the initial use.

In addition, the elastic body for holding the cosmetic according to the present invention is also excellent in retention property (non-absorptive property) of an ultraviolet absorbent included in the cosmetic, and further excellent in durability since "permanent setting due to fatigue" caused by repeated use is small.

Accordingly, the elastic body for holding the cosmetic according to the present invention can be suitably used as a cosmetic-containing elastic body by including the cosmetic in the elastic body for holding the cosmetic, and the cosmetic-containing elastic body can be used in various cosmetic articles.

In addition, when a thermal treatment is applied to a surface of the elastic body for holding the cosmetic according to the present invention, since the surface becomes flat, the cosmetic can be smoothly taken out from the elastic body for holding the cosmetic, for example, by using a puff, and moreover fibrous rubbish can be inhibited from generating in use. In addition, a design and the like also can be applied to the surface of the elastic body from the viewpoint of improvement in decorativeness.

Since the above-mentioned elastic body for holding the cosmetic is used in the cosmetic-containing elastic body according to the present invention, the cosmetic-containing elastic body exhibits effects based on the above-mentioned elastic body for holding the cosmetic. In addition, since the above-mentioned cosmetic-containing elastic body is used in the cosmetic article according to the present invention, the cosmetic article exhibits effects based on the above-mentioned cosmetic-containing elastic body.

The cosmetic which can be used in the cosmetic-containing elastic body according to the present invention includes, for example, foundation, makeup base, eye shadow, eyeliner, mascara, blusher, face powder, eyebrow mascara, cleansing cream, cleansing milk, cleansing liquid, cleansing cream, cleansing foam, massage cream, cold cream, vanishing cream, skin cream, skin gel, milky lotion, skin lotion, essence, various lotions, sunscreen, body cream, body oil, hair shampoo, hair rinse, hair conditioner, hair treatment, hair liquid, a hair tonic and the like, and the present invention is not limited only to those exemplified ones. Among these cosmetics, liquid cosmetic is preferred because the cosmetic-containing elastic body according to the present invention exhibits more excellent effects to the liquid cosmetic.

The viscosity of the cosmetic is not particularly limited. The viscosity of the cosmetic at 25° C. is preferably 500 to 50000 mPa-s, more preferably 500 to 30000 mPa-s, and furthermore preferably 1000 to 20000 mPa-s in the present invention. Incidentally, the viscosity of the cosmetic is a value when determined by using a BM-type viscometer at 25° C.

The amount of the cosmetic used in the cosmetic-containing elastic body according to the present invention cannot be absolutely determined, because the amount differs depending on the kinds of the cosmetic. For example, when the cosmetic is liquid foundation, the liquid foundation having a viscosity of 6000 mPa-s at 25° C. can be used in the cosmetic-containing elastic body having a diameter of 5 cm and a thickness of 1.5 cm in an amount of 10 to 20 g or so.

EXAMPLES

Next, the present invention will be more specifically described in accordance with working examples, and the present invention is not limited only to those examples.

Example 1

A web was produced by blending core-shell conjugated fibers [core component: polyethylene terephthalate, shell component: thermoplastic polyethylene terephthalate, fineness: 6 deniers] and polyester fibers (resin: polyethylene terephthalate, fineness: 3 deniers) in a mass ratio of 70:30 so that respective fibers were arranged to be parallel. The web was heated to melt the shell component under the condition of pressing the web, to give a web sheet (density: 18 kg/m$^3$).

When the web sheet obtained in the above was stretched in a direction of an arrow C shown in FIG. 1(d), stripes based on parallel arrangement of the fibers were observed, whereas when the web sheet was stretched in a direction vertical to the arrow C, stripes were not observed.

Next, a plane face and a side face of the web sheet obtained in the above were observed with an optical microscope. As a result, it was confirmed that a fiber density of the side face of the web sheet was higher than that of the plane face of the web sheet, and that massive (amebic) fused portions were formed at the contacting portions of the constituting fibers.

Next, in accordance with the above-mentioned method A, the web sheet obtained in the above was formed to have a predetermined shape (diameter: 47.5 mm, thickness: 16 mm, density: 18 kg/m$^3$); the formed web sheet was placed in a press laminator (hot press machine); only one side surface of the press laminator was heated to 150° C. for 300 seconds under pressing from the cutting surface so that the thickness of the whole web sheet was 11 mm, to form a dense layer having a thickness of 1.5 mm on one side surface of the web sheet; and thereby an elastic body for holding the cosmetic in which the dense fibrous surface layer made of the above-mentioned web sheet was united into one body with the sparse fibrous substrate made of the above-mentioned web sheet was obtained.

The fibrous surface layer of the above-mentioned web sheet was sliced in a thickness of 1.5 mm, and then a density of the sliced fibrous surface layer was determined. As a result, the density was 46.18 kg/m$^3$. In addition, the sparse fibrous substrate of the above-mentioned web sheet was sliced in a thickness of 1.6 mm, and then a density of the sliced fibrous substrate was determined. As a result, the density was 17.9 kg/m$^3$.

The compression ratio (density of dense fibrous surface layer/density of sparse fibrous substrate) was determined on the basis of the above determined results of the densities. As a result, the compression ratio was 2.58. In addition, an airflow resistance of the dense fibrous surface layer was determined in accordance with the following method. As a result, the airflow resistance was 0.0163 kPa-s/m.

Airflow Resistance

An airflow resistance of a test piece produced by cutting to have a square shape of a length of 50 mm and a width of 50 mm was determined by using an air permeability tester commercially available from KATO TECH CO., LTD. under a product number of KES-F8-AP1.

Figure 2:
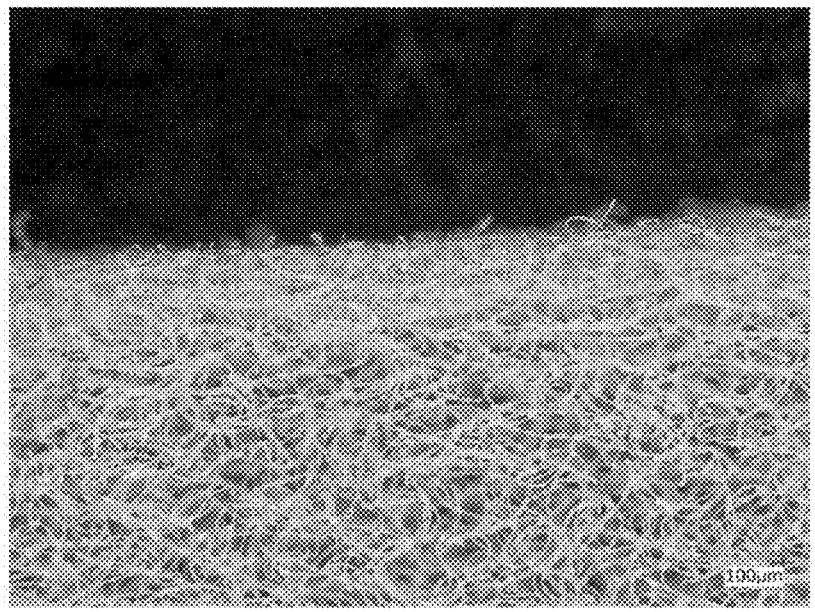
FIG. 2 is an optical microscope photograph in place of a drawing, showing a section of the elastic body for holding the cosmetic obtained in Example 1 in the thickness direction.
Figure 3:
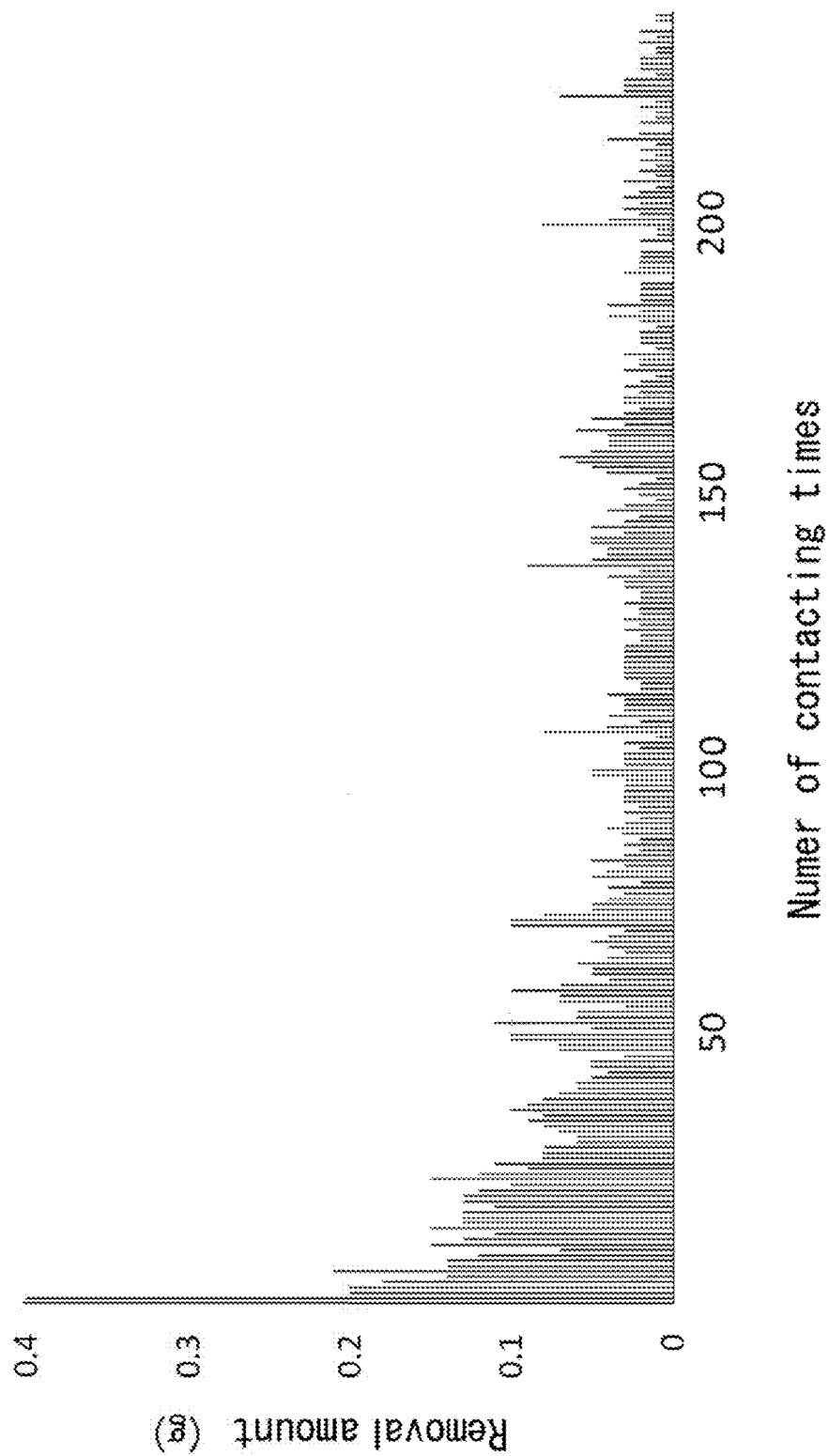
FIG. 3 is a graph showing a result of examination of the relation between the number of removal times (number of contacting times) and a removal amount when the elastic body for holding the cosmetic obtained in Example 1 was examined in Experimental example.
Figure 4:
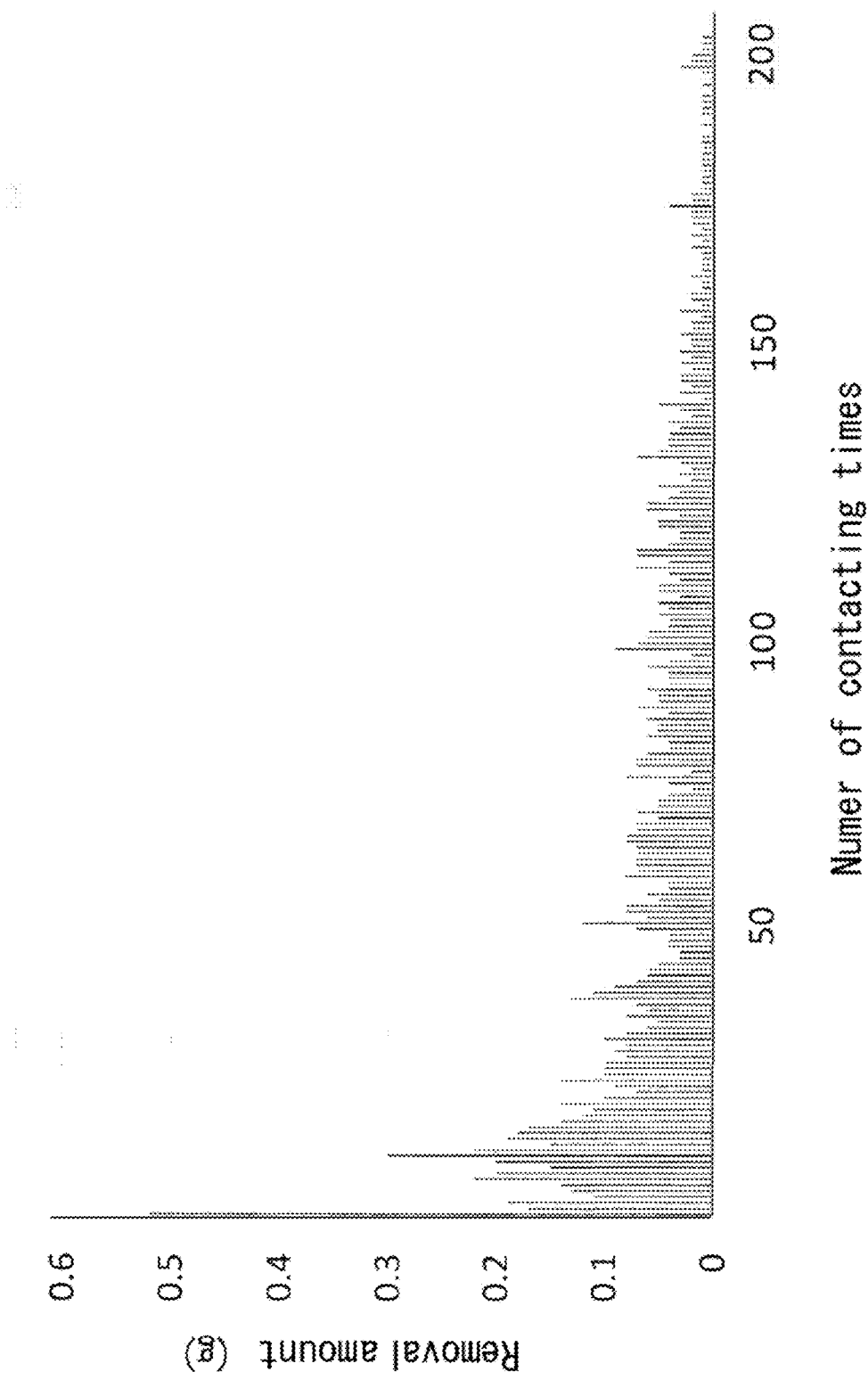
FIG. 4 is a graph showing a result of examination of the relation between the number of removal times (number of contacting times) and a removal amount when the elastic body for holding the cosmetic obtained in Example 2 was examined in Experimental example.
Figure 5:
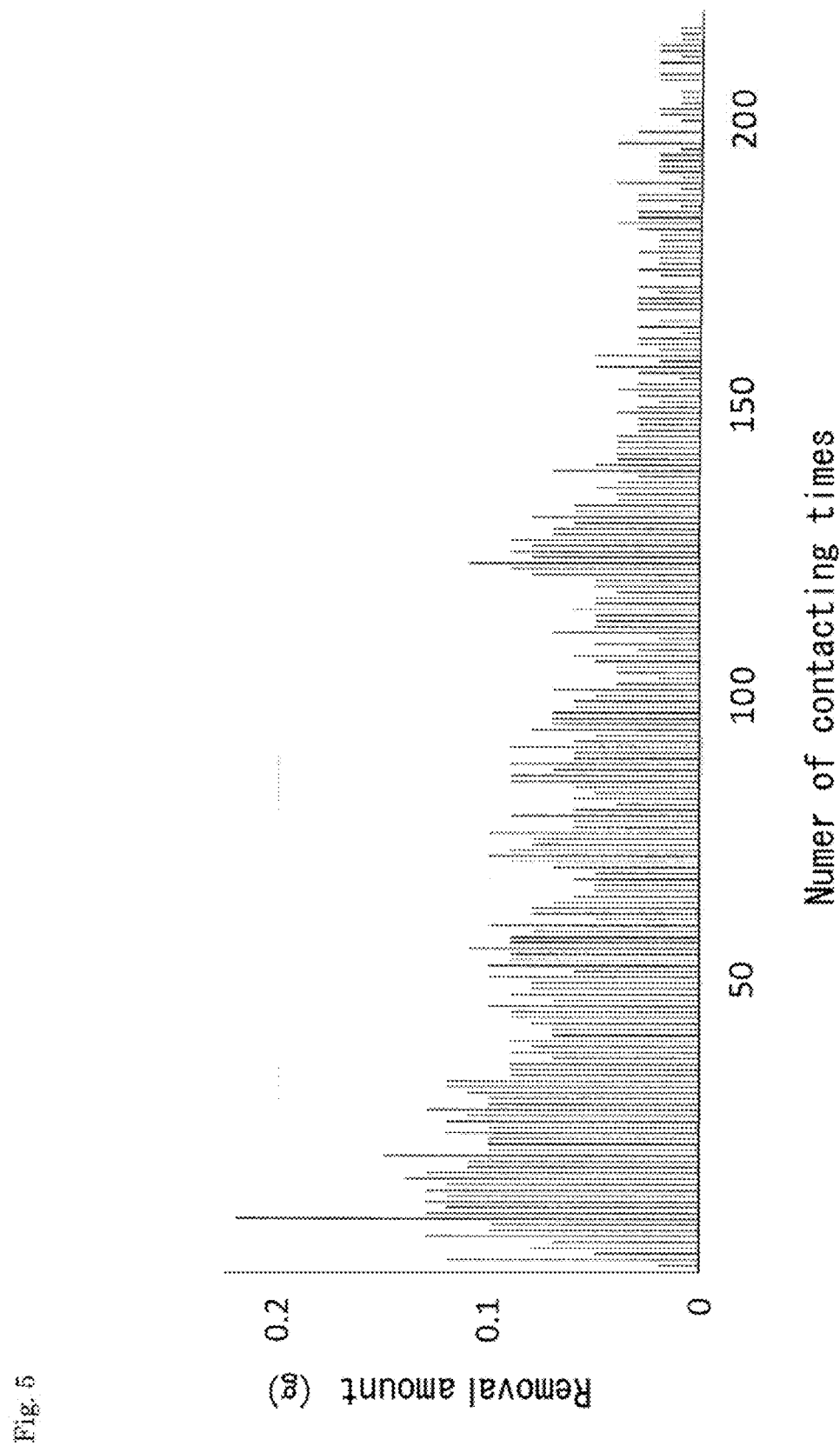
FIG. 5 is a graph showing a result of examination of the relation between the number of removal times (number of contacting times) and a removal amount when the elastic body for holding the cosmetic obtained in Example 3 was examined in Experimental example.
Figure 6:
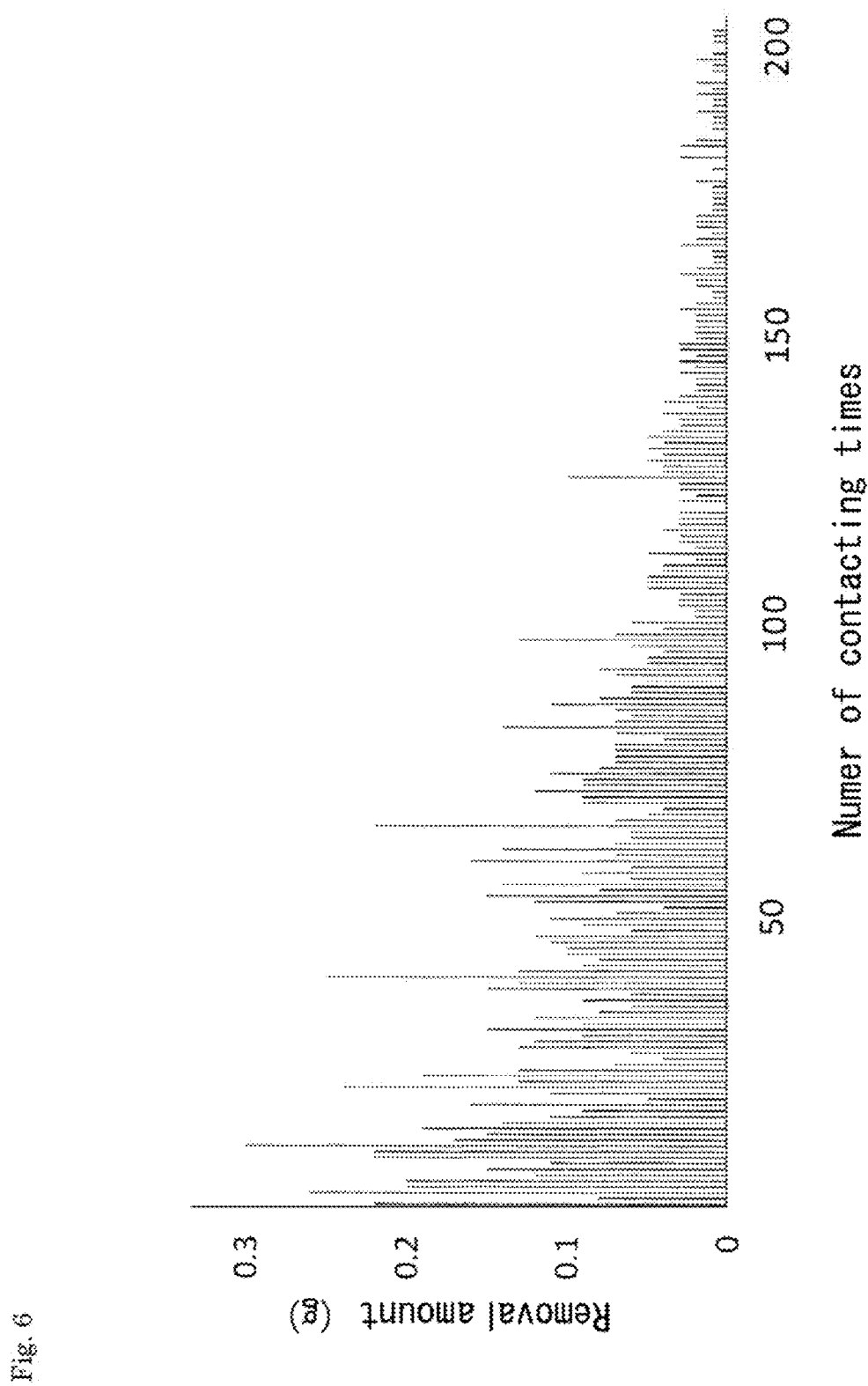
FIG. 6 is a graph showing a result of examination of the relation between the number of removal times (number of contacting times) and a removal amount when the elastic body for holding the cosmetic obtained in Example 4 was examined in Experimental example.
Figure 7:
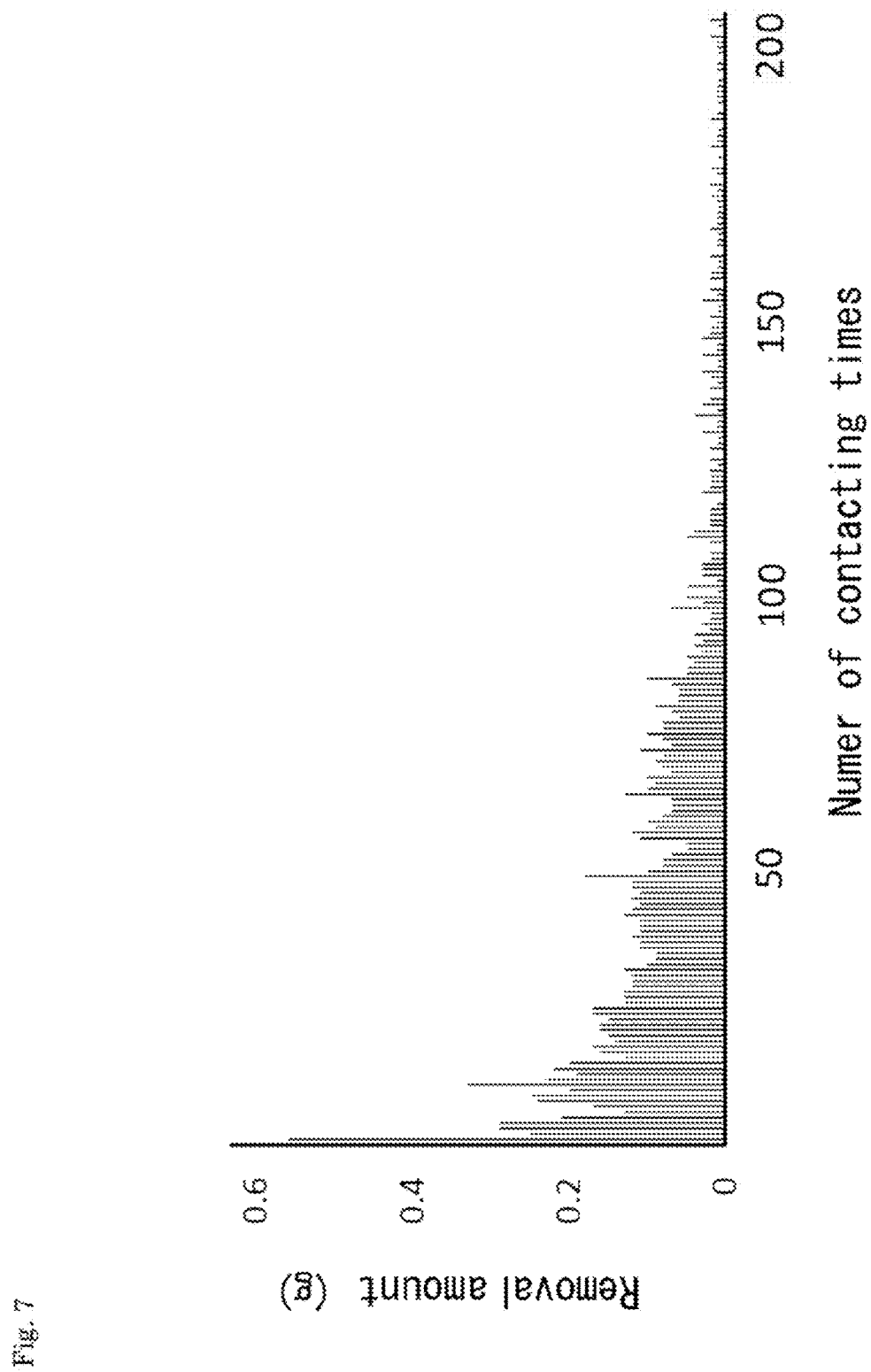
FIG. 7 is a graph showing a result of examination of the relation between the number of removal times (number of contacting times) and a removal amount when the elastic body for holding the cosmetic obtained in Example 5 was examined in Experimental example.
Figure 8:
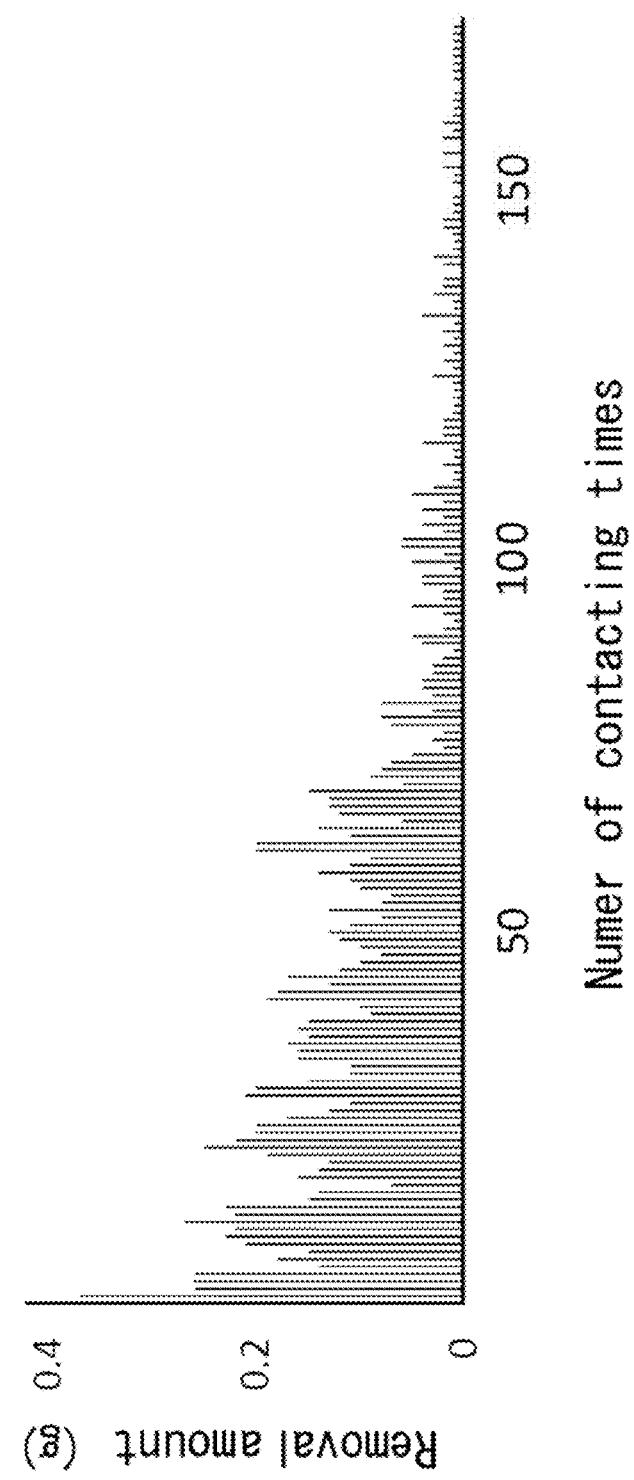
FIG. 8 is a graph showing a result of examination of the relation between the number of removal times (number of contacting times) and a removal amount when the elastic body for holding the cosmetic obtained in Example 6 was examined in Experimental example.
Figure 9:
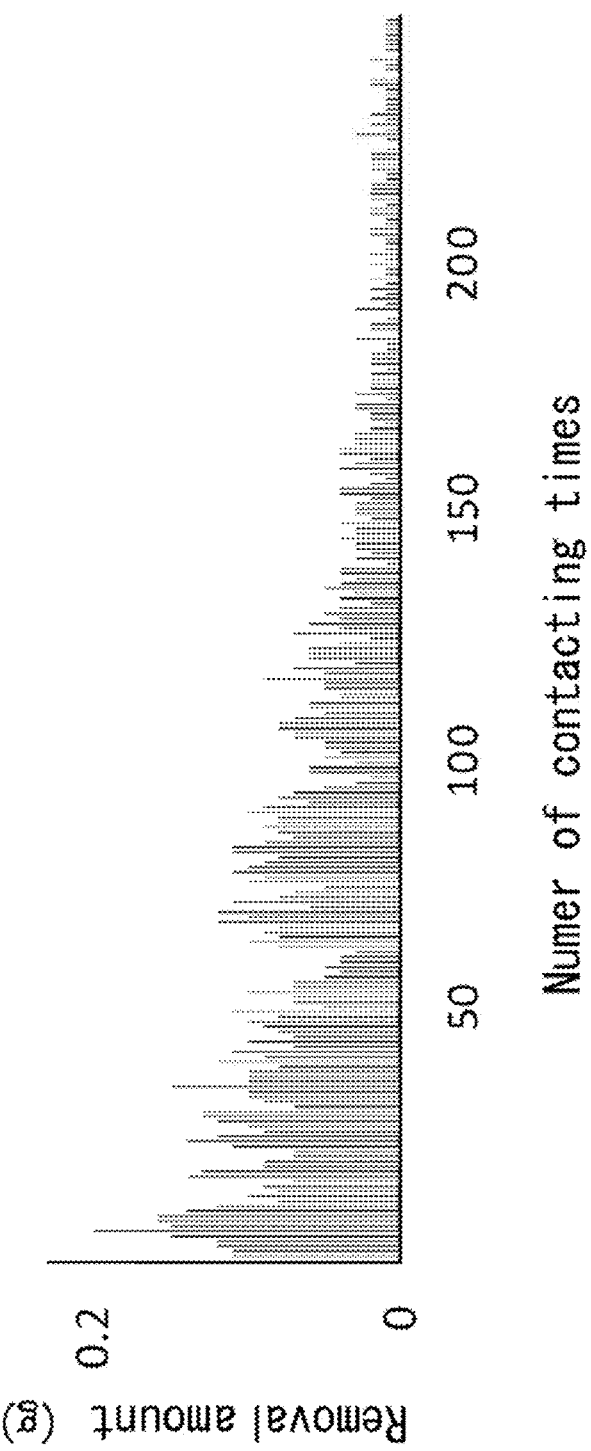
FIG. 9 is a graph showing a result of examination of the relation between the number of removal times (number of contacting times) and a removal amount when the elastic body for holding the cosmetic obtained in Example 7 was examined in Experimental example.
Figure 10:
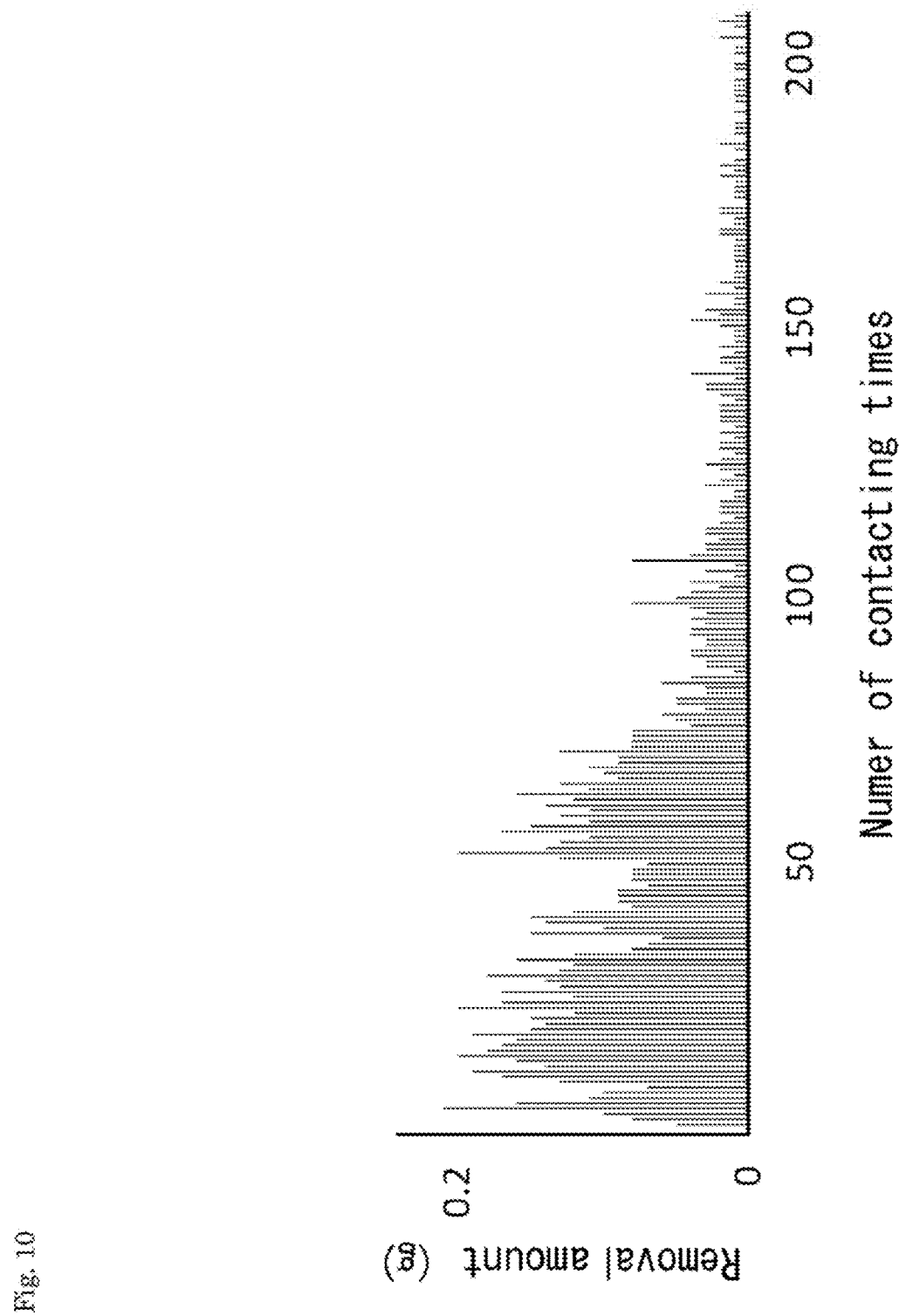
FIG. 10 is a graph showing a result of examination of the relation between the number of removal times (number of contacting times) and a removal amount when the elastic body for holding the cosmetic obtained in Example 8 was examined in Experimental example.
Figure 11:
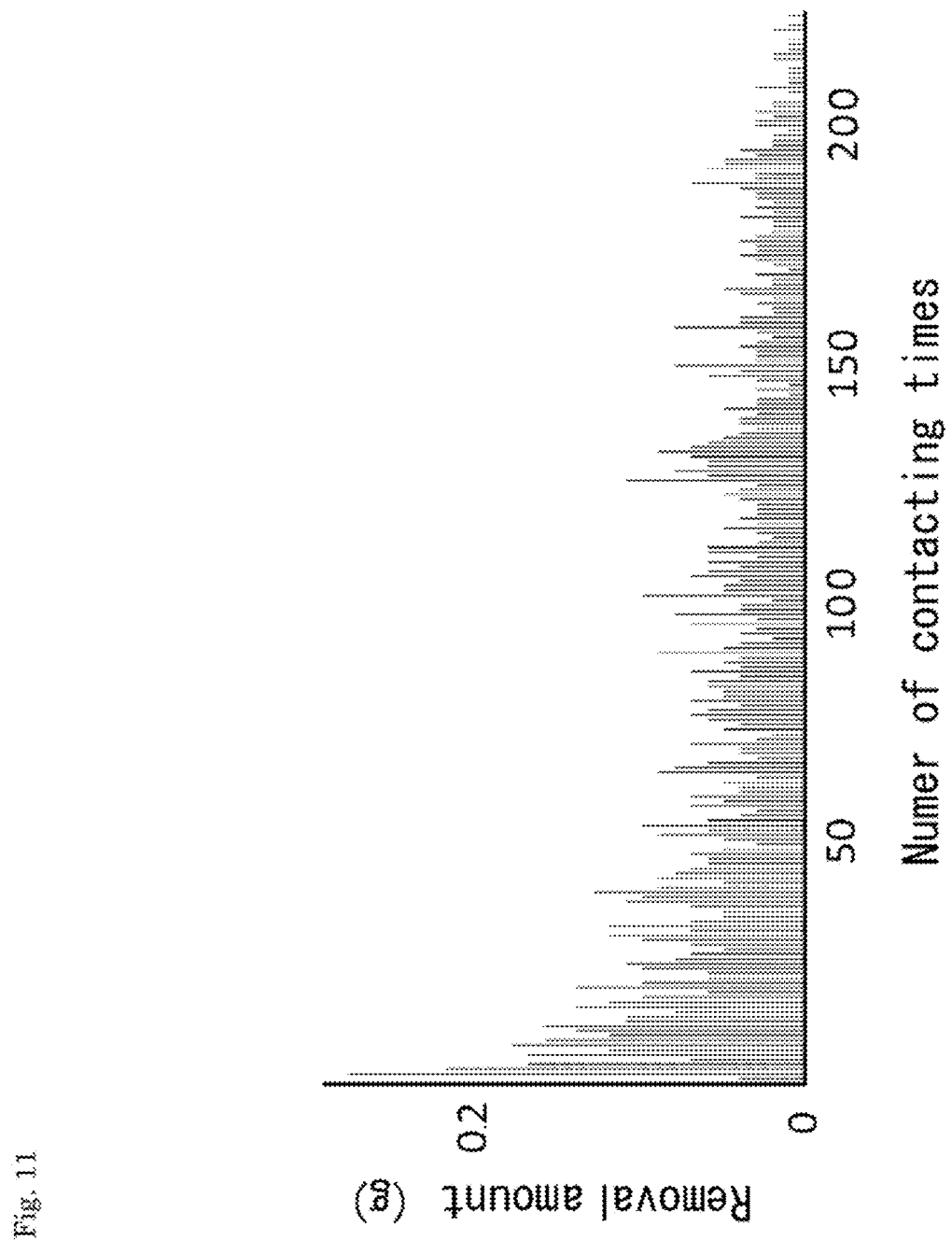
FIG. 11 is a graph showing a result of examination of the relation between the number of removal times (number of contacting times) and a removal amount when the elastic body for holding the cosmetic obtained in Example 9 was examined in Experimental example.
Figure 12:
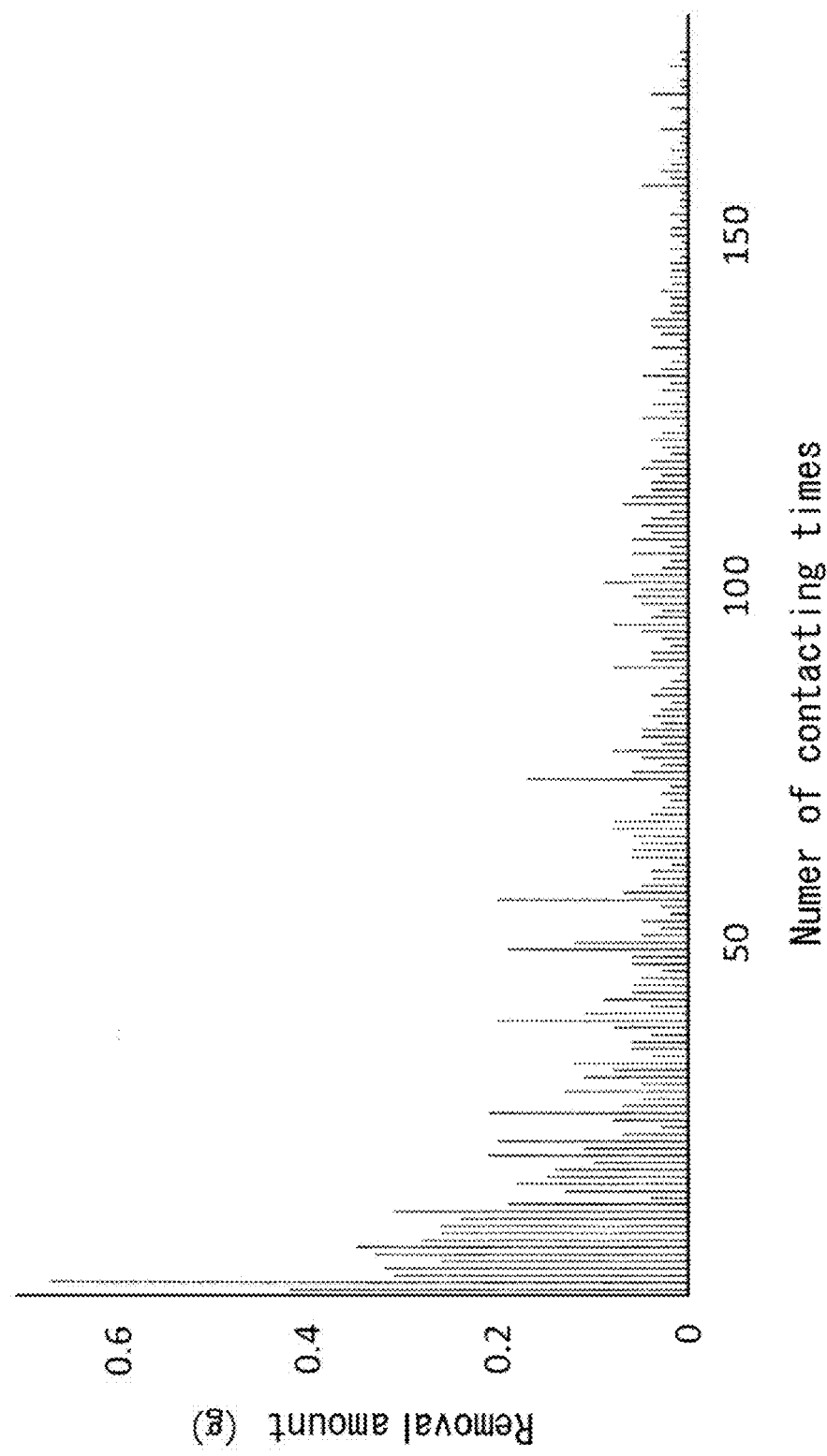
FIG. 12 is a graph showing a result of examination of the relation between the number of removal times (number of contacting times) and a removal amount when the elastic body for holding the cosmetic obtained in Comparative Example 1 was examined in Experimental example.
Figure 13:
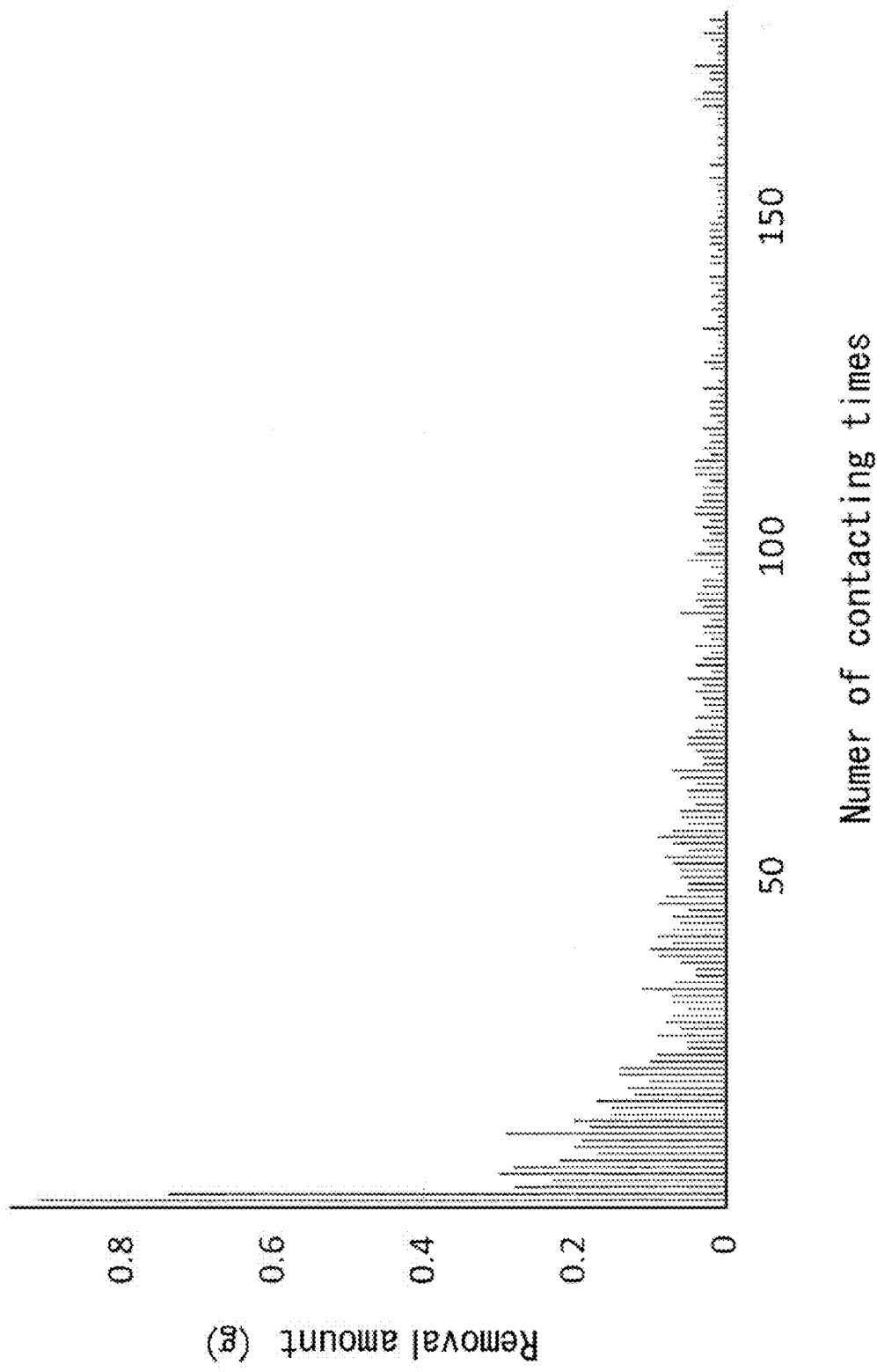
FIG. 13 is a graph showing a result of examination of the relation between the number of removal times (number of contacting times) and a removal amount when the elastic body for holding the cosmetic obtained in Comparative Example 2 was examined in Experimental example.
Figure 14:
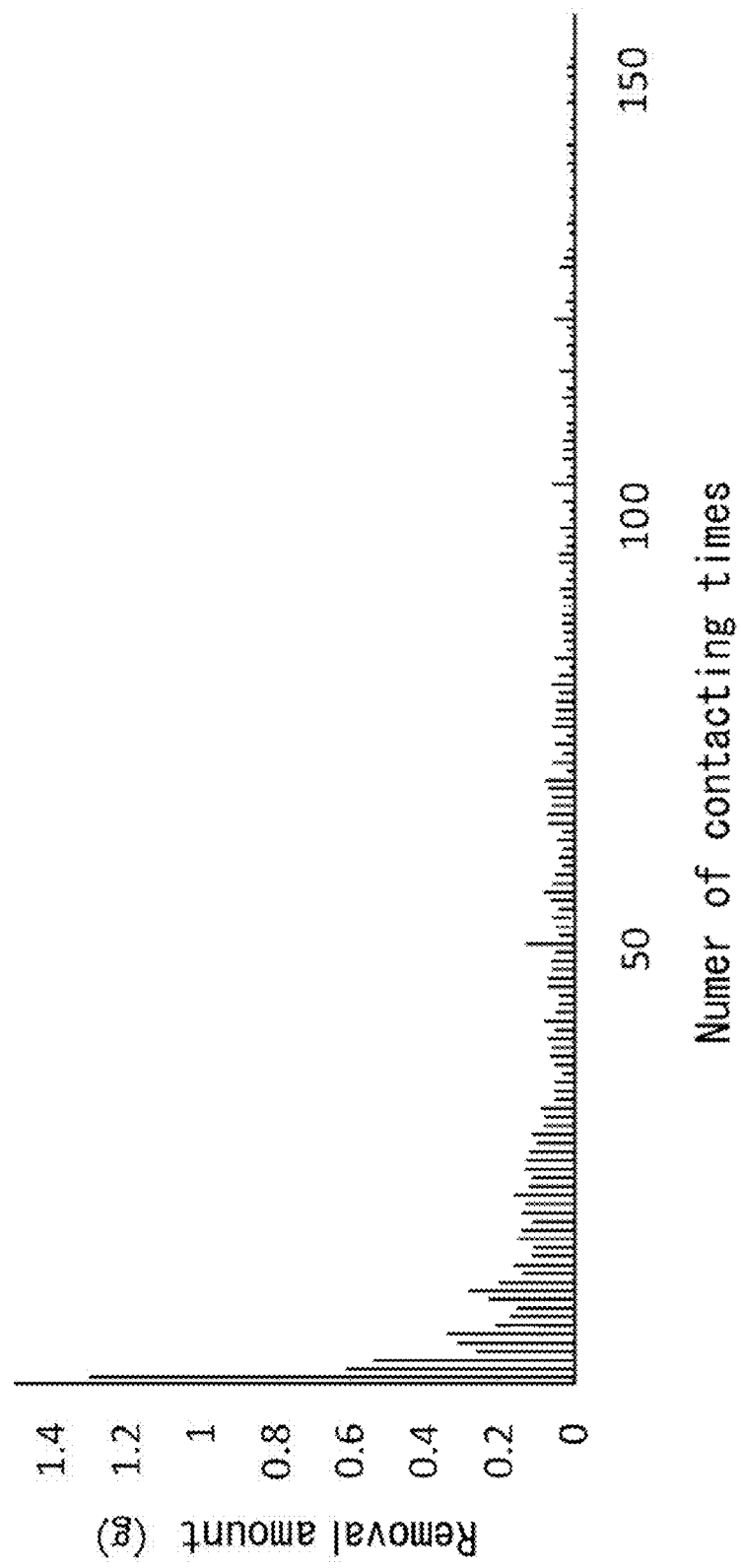
FIG. 14 is a graph showing a result of examination of the relation between the number of removal times (number of contacting times) and a removal amount when the elastic body for holding the cosmetic obtained in Comparative Example 3 was examined in Experimental example.

The side face of the elastic body for holding the cosmetic obtained in the above was observed with an optical microscope. Its result was shown in FIG. 2. FIG. 2 is an optical microscope photograph showing a section of the elastic body for holding the cosmetic obtained in the above in the thickness direction of the elastic body. Incidentally, the scale bar of the microscope photograph is shown in the right lower part of the microscope photograph, and the length of the scale bar means 100 μm.

From the results shown in FIG. 2, it can be seen that the dense fibrous surface layer is formed on the surface of the elastic body for holding the cosmetic obtained in the above, and that the sparse fibrous substrate is continuously formed under the fibrous surface layer.

Example 2

A web sheet (diameter: 47.5 mm, thickness: 20 mm, density: 18 kg/m$^3$) similar to the web sheet used in Example 1 was formed by the above-mentioned method A, and the web sheet was placed in the press laminator (hot press machine). Only one side surface of the press laminator was heated to 150° C. for 450 seconds under pressing the web sheet from the cutting surface so that the thickness of the whole web sheet was 11 mm, to form a dense layer having a thickness of 1.5 mm on one side surface of the web sheet, and thereby an elastic body for holding the cosmetic in which the dense fibrous surface layer made of the above-mentioned web sheet was united into one body with the sparse fibrous substrate made of the above-mentioned web sheet was obtained.

The fibrous surface layer of the above-mentioned web sheet was sliced in a thickness of 1.5 mm, and then a density of the sliced fibrous surface layer was determined. As a result, the density was 58.4 kg/m$^3$. In addition, the sparse fibrous substrate of the above-mentioned web sheet was sliced so as to have a thickness of 1.6 mm, and then a density of the sliced fibrous substrate was determined. As a result, the density was 18.2 kg/m$^3$.

The compression ratio (density of dense fibrous surface layer/density of sparse fibrous substrate) was determined on the basis of the above determined results of the densities. As a result, the compression ratio was 2.58. In addition, an airflow resistance of the dense fibrous surface layer was determined in the same manner as in Example 1. As a result, the airflow resistance was 0.0163 kPa-s/m.

Example 3

A web was produced by blending core-shell conjugated fibers [core component: polyethylene terephthalate, shell component: thermoplastic polyethylene terephthalate, fineness: 6 deniers] and polyester fibers (resin: polyethylene terephthalate, fineness: 3 deniers) in a mass ratio of 70:30 so that respective fibers were arranged to be parallel. The web was heated to melt the shell component under the condition of pressing the web, to give a web sheet (density: 20 kg/m$^3$). The density of this web sheet was 20.2 kg/m$^3$.

The web sheet obtained in the above was sliced so as to have a thickness of 8 mm, and then the sliced web sheet was placed in the press laminator (hot press machine). Only one side surface of the press laminator was heated to 219° C. for 72 seconds under pressing the above-mentioned web sheet from the sliced face so that the thickness of the web was 4 mm. Thereafter, a dense fibrous surface layer having a diameter of 47.5 mm was punched out from the web sheet. The density of the dense fibrous surface layer obtained in the above was 40.7 kg/m$^3$. The compression ratio (density of dense fibrous surface layer/density of sparse fibrous substrate) was determined on the basis of the above determined results of the densities. As a result, the compression ratio was 2.01. In addition, an airflow resistance of the dense fibrous surface layer was determined in the same manner as in Example 1. As a result, the airflow resistance was 0.0377 kPa·s/m.

A web was produced by blending core-shell conjugated fibers [core component: polyethylene terephthalate, shell component: thermoplastic polyethylene terephthalate, fineness: 6 deniers] and polyester fibers (resin: polyethylene terephthalate, fineness: 3 deniers) in a mass ratio of 70:30 so that respective fibers were arranged to be parallel. The web was heated to melt the shell component under the condition of pressing the web, to give a web sheet (density: 18 kg/m$^3$). The web sheet obtained in the above was cut, to give a sparse fibrous surface layer having a diameter of 47.5 mm and a thickness of 9 mm.

Nest, the dense fibrous surface layer obtained in the above was placed on the sparse fibrous surface layer obtained in the above, to give an elastic body for holding the cosmetic.

Example 4

A web sheet (density: 20 kg/m$^3$) similar to the web sheet used in Example 3 was sliced so as to have a thickness of 4 mm, and the sliced web sheet (density: 20.2 kg/m$^3$) was placed in the press laminator (hot press machine). Only one side surface of the press laminator was heated to 219° C. for 72 seconds under pressing the web sheet from the sliced face so that the web sheet had a thickness of 3 mm. A dense fibrous surface layer having a diameter of 47.5 mm was punched out from the web sheet. The density of the dense fibrous surface layer was 27.5 kg/m$^3$. The compression ratio (density of dense fibrous surface layer/density of sparse fibrous substrate) was determined on the basis of the above-mentioned determined results of the densities. As a result, the compression ratio was 1.36. In addition, an airflow resistance of the dense fibrous surface layer was determined in the same manner as in Example 1. As a result, the airflow resistance was 0.0117 kPa·s/m.

Next, the dense fibrous surface layer obtained in the above was placed on the web sheet (diameter: 47.5 mm, thickness: 9 mm, density: 18 kg/m$^3$) in the same manner as in Example 3, to give an elastic body for holding the cosmetic.

Example 5

A web sheet (diameter: 47.5 mm, thickness: 15 mm, density: 18 kg/m$^3$) similar to the web sheet used in Example 1 was formed by the above-mentioned method A, and the web sheet was placed in the press laminator (hot press machine). Only one side surface of the press laminator was heated to 150° C. for 450 seconds under pressing the web sheet from the cutting surface so that the thickness of the whole web sheet was 11 mm, to form a dense layer having a thickness of 1.5 mm on one side surface of the web sheet, and thereby an elastic body for holding the cosmetic in which the dense fibrous surface layer made of the above-mentioned web sheet was united into one body with the sparse fibrous substrate made of the above-mentioned web sheet was obtained.

Example 6

A web sheet (diameter: 47.5 mm, thickness: 12 mm, density: 18 kg/m$^3$) similar to the web sheet used in Example 1 was formed by the above-mentioned method A, and the web sheet was placed in the press laminator (hot press machine). Only one side surface of the press laminator was heated to 150° C. for 450 seconds under pressing the web sheet from the cutting surface so that the thickness of the whole web sheet was 11 mm, to form a dense layer having a thickness of 0.5 mm on one side surface of the web sheet, and thereby an elastic body for holding the cosmetic in which the dense fibrous surface layer made of the above-mentioned web sheet was united into one body with the sparse fibrous substrate made of the above-mentioned web sheet was obtained.

Example 7

A web sheet (density: 20 kg/m$^3$) similar to the web sheet used in Example 3 was sliced so as to have a thickness of 6 mm, and the sliced web sheet (density: 20.2 kg/m$^3$) was placed in the press laminator (hot press machine). Only one side surface of the press laminator was heated to 220° C. for 72 seconds under pressing the web sheet from the sliced face so that the thickness of the web sheet was 4 mm. A dense fibrous layer having a diameter of 47.5 mm was punched out from the web sheet.

Next, the dense fibrous layer obtained in the above was placed on a web sheet (diameter: 47.5 mm, thickness: 9 mm, density: 18 kg/m$^3$) in the same manner as in Example 3, and thereby an elastic body for holding the cosmetic was obtained.

Example 8

A web sheet (density: 20 kg/m$^3$) similar to the web sheet used in Example 3 was sliced so as to have a thickness of 4 mm, and the sliced web sheet (density: 20.2 kg/m$^3$) was placed in the press laminator (hot press machine). Only one side surface of the press laminator was heated to 220° C. for 72 seconds under pressing the web sheet from the sliced face so that the thickness of the web sheet was 2.8 mm. A dense fibrous layer having a diameter of 47.5 mm was punched out from the web sheet.

Next, the dense fibrous layer obtained in the above was placed on a web sheet (diameter: 47.5 mm, thickness: 9 mm, density: 18 kg/m$^3$) in the same manner as in Example 3, and thereby an elastic body for holding the cosmetic was obtained.

Example 9

A web sheet (density: 20 kg/m$^3$) similar to the web sheet used in Example 3 was sliced so as to have a thickness of 4 mm, and the sliced web sheet (density: 20.2 kg/m$^3$) was placed in the press laminator (hot press machine). Only one side surface of the press laminator was heated to 220° C. for 72 seconds under pressing the web sheet from the sliced face so that the thickness of the web sheet was 2 mm. A dense fibrous layer having a diameter of 47.5 mm was punched out from the web sheet.

Next, the dense fibrous layer obtained in the above was placed on a web sheet (diameter: 47.5 mm, thickness: 9 mm, density: 18 kg/m³) in the same manner as in Example 3, and thereby an elastic body for holding the cosmetic was obtained.

Comparative Example 1

A web was produced by blending core-shell conjugated fibers [core component: polyethylene terephthalate, shell component: thermoplastic polyethylene terephthalate, fineness: 6 deniers] and polyester fibers (resin: polyethylene terephthalate, fineness: 3 deniers) in a mass ratio of 70:30 so that respective fibers were arranged to be parallel. The web was heated to melt the shell component under the condition of pressing the web, to give a web sheet (density: 18 kg/m³).

An elastic body for holding the cosmetic, in which its surface was not processed, was cut out from the web sheet obtained in the above so as to have a diameter of 47.5 mm and a thickness of 12 mm.

Comparative Example 2

An elastic body for holding the cosmetic made of a polyether-based polyurethane foam and having a diameter of 47.5 mm and a thickness of 12 mm was prepared.

Comparative Example 3

An elastic body for holding the cosmetic made of nitrile rubber (NBR) sponge and having a diameter of 47.5 mm and a thickness of 12 mm was prepared.

Experimental Example

A mineral water foundation commercially available from Shiseido Company, Limited was impregnated in the elastic body for holding the cosmetic obtained in each of Examples and Comparative examples in an amount of 15 g, and the elastic body for holding the cosmetic was allowed to stand for one hour, to give a test sample. The mineral water foundation included in the test sample obtained in the above was wiped off with a puff in a pressing force in actual use (human strength), and the mineral water foundation being wiped off with the puff was transferred to a nonwoven fabric so that the mineral water foundation included in the puff was sufficiently removed from the puff. This operation was repeated, and finished when the decrease of the removal amount of the cosmetic was not observed three times.

The amount of the mineral water foundation being wiped off with the puff (hereinafter referred to as "removal amount") was obtained from the equation:

[Removal amount (g)]=[mass (g) of the test sample before wiping off]−[mass (g) of the test sample after wiping off].

The relation between the number of removal times (number of contacting times) of the elastic body for holding the cosmetic obtained in each of Examples 1 to 9 and Comparative examples 1 to 3 and the removal amount was examined. Its results are shown in FIGS. 3 to 14 in this order. Incidentally, the term "number of contacting times" means that number of times for wiping off the mineral water foundation with a puff.

As shown in the results of FIGS. 3 to 14, it can be seen that the elastic body for holding the cosmetic obtained in each Example exhibits excellent effects such that the elastic body for holding the cosmetic can suppress that the cosmetic included in the elastic body for holding the cosmetic is taken out from the elastic body in a large amount at a time at the initial stage of use, and that the elastic body for holding the cosmetic can increase the number of times capable of using the cosmetic since the cosmetic can be taken out from the elastic body for holding the cosmetic in an amount suitable for one use from the initial stage of its use.

In addition, when the repeat of the above-mentioned operation for the elastic body for holding the cosmetic obtained in each Example was finished, the elastic body for holding the cosmetic was observed with naked eyes. As a result, permanent setting due to fatigue was hardly observed in each of the elastic bodies for holding the cosmetic. From this fact, it can be seen that the elastic body for holding the cosmetic obtained in each Example is small in permanent setting due to fatigue even when the elastic body is continuously used.

INDUSTRIAL APPLICABILITY

Since the elastic body for holding the cosmetic according to the present invention exhibits excellent effects such that the elastic body can suppress that the cosmetic included in the elastic body is taken out from the elastic body in a large amount at a time at the initial stage of use, the elastic body can be suitably used in the cosmetic article, in particular the cosmetic article in which liquid cosmetic is impregnated, such as a liquid cosmetic article for make-up (for example, liquid foundation, cheek and the like).

EXPLANATIONS OF REFERENTIAL NUMBERS

1 Web
2 Web sheet

The invention claimed is:

1. An elastic body for holding a cosmetic, having a three-dimensional structure,
   wherein said elastic body has a dense fibrous surface layer and a sparse fibrous substrate,
   wherein each of the dense fibrous surface layer and the sparse fibrous substrate comprises a web sheet comprising (a) a web comprising a conjugated fiber containing a resin A and a resin B, in which a melting temperature of the resin A is lower than a melting temperature of the resin B, and (b) a synthetic fiber; and constituent fibers of the web are fused to be united into one body at their contacting portions by the resin A, and
   wherein the conjugated fiber and the synthetic fiber are arranged in parallel in the thickness direction of the elastic body for holding a cosmetic.

2. The elastic body for holding a cosmetic according to claim 1, wherein the dense fibrous surface layer and the sparse fibrous substrate are united into one body, or the dense fibrous surface layer is placed on the sparse fibrous substrate.

3. The elastic body for holding a cosmetic according to claim 1, wherein a mass ratio of the conjugated fiber to the synthetic fiber (conjugated fiber/synthetic fiber) is 30/70 to 80/20.

4. The elastic body for holding a cosmetic according to claim 1, wherein the synthetic fiber is a polyester fiber.

5. The elastic body for holding a cosmetic according to claim 3, wherein the dense fibrous surface layer and the sparse fibrous substrate are united into one body, and the dense fibrous surface layer has a density of 45 to 80 kg/m$^3$, and the sparse fibrous substrate has a density of 13 to 20 kg/m$^3$.

6. The elastic body for holding a cosmetic according to claim 5, wherein a value obtained by dividing the density of the dense fibrous surface layer by the density of the sparse fibrous substrate is 2 to 4.

7. The elastic body for holding a cosmetic according to claim 2, wherein the dense fibrous surface layer is placed on the sparse fibrous substrate, and the dense fibrous surface layer has a density of 25 to 45 kg/m$^3$, and the sparse fibrous substrate has a density of 15 to 22.5 kg/m$^3$.

8. The elastic body for holding a cosmetic according to claim 7, wherein a value obtained by dividing the density of the dense fibrous surface layer by the density of the sparse fibrous substrate is 1.2 to 2.5.

9. A cosmetic-containing elastic body comprising the elastic body for holding a cosmetic according to claim 1 and a cosmetic, wherein the cosmetic is included in the elastic body for holding a cosmetic.

10. A cosmetic article comprising the cosmetic-containing elastic body according to claim 9.

\* \* \* \* \*